US006387879B1

(12) United States Patent
Blume et al.

(10) Patent No.: US 6,387,879 B1
(45) Date of Patent: May 14, 2002

(54) COMPOUNDS THAT BIND GROWTH TO HORMONE RECEPTOR

(75) Inventors: Arthur J. Blume, Annandale; Renee Brissette, Edison, both of NJ (US); Juan Carcamo, New York, NY (US); Wlodek S. Mandecki, Libertyville, IL (US); Pauline M. Tang, Bridgewater, NJ (US)

(73) Assignee: DGI Biotechnologies, Inc., Edison, NJ (US)

( * ) Notice: Subject to any disclaimer, the term of this patent is extended or adjusted under 35 U.S.C. 154(b) by 0 days.

(21) Appl. No.: 08/990,888

(22) Filed: Dec. 15, 1997

(51) Int. Cl.[7] .............................................. A61K 38/04

(52) U.S. Cl. .................. 514/13; 424/193.1; 424/198.1; 530/300; 530/326; 530/399

(58) Field of Search ................................ 530/300, 326, 530/399, 387.9, 388.22, 386.25, 389.2, 389.3; 435/69.1; 424/143.1, 198.1; 514/13

(56) References Cited

PUBLICATIONS

J.F. Hocquette et al., Endocrinology 127(4):1665–1672, 1990.*

Y. Saito et al., Biological and Pharmaceutical Bulletin (Japan), 17(7):983–986, 1994.*

C. Andersson et al., Int. J. Peptide and Protein Res. 47(4):311–321, Apr. 1996.* degli Uberti EC, Trasforini G, Salvadori S, Margutti A, Tomatis R, Rotola C, Bianconi M, Pansini R. "Stimulatory effect of dermorphin, a new synthetic potent opiate–like peptide, on human growth hormone secretion" *Neuroendocrinology*. 1983 Oct;37(4):280–3.

Livnah O, Stura EA, Johnson DL, Middleton SA, Mulcahy LS, Wrighton NC, Dower WJ, Jolliffe LK, Wilson IA. "Functional mimicry of a protein hormone by a peptide agonist: the EPO receptor complex at 2.8 A." *Science*. Jul. 26, 1996; 273(5274):464–71.

Eason MG, Francis RS, Kuhn CM. "mu–Opioid agonists stimulate growth hormone secretion in immature rats" *Neuroendocrinology*. Jun. 1996; 63(6):489–97.

Muruais J, Penalva A, Dieguez C, Casanueva FF. "Influence of endogenous cholinergic tone and alpha–adrenergic pathways on growth hormone responses to His–D–Trp–Ala–Trp–D–Phe–Lys–NH2 in the dog" *J Endocrinol*. Aug. 1993; 138(2);211–8.

Wells JA. "Hormone mimicry" *Science*. Jul. 26, 1996; 273(5274):449–50.

Moore GJ. "Discovery and design of peptide mimetics" *Proc West Pharmacol Soc*. 1997;40:115–9.

Wrighton NC, Farrell FX, Chang R, Kashyap AK, Barbone FP, Mulcahy LS, Johnson DL, Barrett RW, Jolliffe LK, Dower WJ. "Small Peptides as potent mimetics of the protein hormone erythropoietin" *Science*. Jul. 26, 1996; 273(5274):458–64.

Braisted A. "Hormone peptidomimetics: seeing double" *Nat Biotechnol*. Nov. 1997; 15(12):1244–5.

Hruby VJ, Ahn JM, Liao S. "Synthesis of oligopeptide and peptidomimetic libraries" *Curr Opin Chem Biol*. Jun. 1997; 1(1):114–9.

Kieber–Emmons T, Murali R, Greene MI. "Therapeutic peptides and peptidomimetics" *Curr Opin Biotechnol*. Aug. 1997; 8(4):435–41.

Yanofsky SD, Baldwin DN, Butler JH, Holden FR, Jacobs JW, Balasubramanian P, Chinn JP, Cwirla SE, Peters–Bhatt E, Whitehorn EA, Tate EH, Akeson A, Bowlin TL, Dower WJ, Barrett RW. "High affinity type I interleukin 1 receptor antagonists discovered by screening recombinant peptide libraries" *Proc Natl Acad Sci U S A*. Jul. 9, 1996; 93(14):7381–6.

Cwirla SE, Balasubramanian P, Duffin DJ, Wagstrom CR, Gates CM, Singer SC, Davis AM, Tansik RL, Mattheakis LC, Boytos CM, Schatz PJ, Baccanari DP, Wrighton NC, Barrett RW, Dower WJ. "Peptide agonist of the thrombopoietin receptor as potent as the natural cytokine" *Science*. Jun. 13, 1997; 276(5319):1696–9.

Katz BA. "Structural and mechanistic determinants of affinity and specificity of ligands discovered or engineered by phage display" *Annu Rev Biophys Biomol Struct*. 1997;26:27–45.

F. Martin, C. Toniatti, A.L. Salvati, S. Venturini, G. Ciliberto, R. Cortese, M. Sollazo, 1994, "The affinity–selection of minibody polypeptide inhibitor of human interleukin–6" *EMBO J*. 13:5303–5309.

B.S. Wang, A.L. Lumanglas, C.A. Bona, T.M. Moran, 1996, "Functional characterization of monoclonal antibodies specific to growth hormone receptor" *Mol. Immunol.* 33:1197–1202.

C.D. Partidos, C.L. Chirinos–Rojas, M.W. Steward, 1997, "The potential of combinatorial peptide libraries for the identification of inhibitors of TNF–α mediated cytotoxicity in vitro" *Immunol. Lett.* 57:113–116.

S.C. Souza, G.P. Frick, X. Wang, J.J. Kopchick, R.B. Lobo, H.M. Goodman, 1995, "A single arginine residue determines species specificity of the human growth hormone" *Proc. Natl. Acad. Sci. USA* 92:959–963.

Z. Guo, D. Zhou, P.G. Schultz, 2000, "Designing small––molecule switches for protein–protein interactions" *Science* 288:2042–2045.

* cited by examiner

*Primary Examiner*—Lorraine Spector
(74) *Attorney, Agent, or Firm*—Morgan & Finnegan, LLP

(57) ABSTRACT

The present invention provides peptides that bind to the active site of the growth hormone receptor. The present invention also provides methods of using these peptides to identify small organic molecules, which are novel agonists or antagonists of the growth hormone receptor. In addition, the present invention provides kits and therapeutic compositions comprising the peptides that bind to growth hormone receptor.

33 Claims, 20 Drawing Sheets

Binders

L C Q S L G V T Y P G W L A G W C A (SEQ ID NO:16)

M $^{28}$R $^{2}$W $^{2}$Q $^{6}$I $^{22}$G $^{47}$W V $^{7}$T A $^{2}$G $^{2}$T F A $^{5}$A $^{8}$S $^{3}$F I $^{3}$V $^{2}$S $^{2}$N E $^{d}$D $^{5}$R $^{2}$S R

A P $^{3}$L $^{4}$K $^{2}$W

V $^{2}$P $^{2}$A D

R E $^{2}$N

F W

L

Consensus

L C Q R L G I G W P G W L A G W C A (SEQ ID NO:63)

T A S T

D R V

L K

Pepitdes

| | | | |
|---|---|---|---|
| ● | control | DYKDWCLTLQPLVWASGGGYCA | (SEQ ID NO:10) |
| ○ | H5 WT | DYKDLCQSLGVTYPGWLAGWCA | (SEQ ID NO:8) |
| ■ | H5-447 | DYKDLCQRLGVGWPGWLSGWCA | (SEQ ID NO:11) |
| □ | H5-418 | DYKDLCQSWQVTWPGWLAGWCA | (SEQ ID NO:12) |
| ⊜ | H5-445 | DYKDLCQRLGVGWPGWLAGWCA | (SEQ ID NO:13) |
| ⦶ | H5-443 | DYKDLCQRLGVTWPGWLAGWCA | (SEQ ID NO:14) |

| PEPTIDES | SEQ ID NO | ROUND 1 | ROUND 2 | ROUND 3 | ROUND 4 |
|---|---|---|---|---|---|
| LCQSLGVTYPGWLAGWCA | 16 | 9 | 16 | 7 | 1 |
| LCQSLG**I**TYPGWLAGWCA | 17 | 2 | 2 | | |
| LCQ**T**LGVTYPGWLAGWCA | 18 | 1 | | | |
| LCQSLGV**K**YPGWLAGWCA | 19 | 1 | | | |
| LCQSLGV**K**YPGWL**T**GWCA | 20 | 1 | | | |
| LCQSLGVTYPGWL**S**GWCA | 21 | 1 | | | |
| LCQSLGV**A**YPGWLAGWCA | 22 | 1 | | | |
| LCQSLGVT**F**PGWL**S**GWCA | 23 | 1 | | | |
| LCQ**A**LGVTYPGWLAGWCA | 24 | 1 | 1 | | |
| LCQSLGV**S**YPGWLAGWCA | 25 | 2 | | | |
| LCQSLGVTYPGWLA**A**WC**R** | 26 | 1 | | | |
| LCQSLGVTYPGWL**D**GWCA | 27 | | 1 | | |
| LCQSLGV**S**YPGWL**V**GWCA | 28 | | 1 | | |
| LCQ**T**LGV**K**YPGWLAGWCA | 29 | | 1 | | |
| LCQSLG**L**TYPGWLAGWC**G** | 30 | | 1 | | |
| LCQSLG**EA**YPGWLAGWCA | 31 | | 1 | | |
| LCQ**R**LG**L**T**W**PGWLAGWCA | 32 | | 1 | | |
| LCQSLGV**WW**PGWLAGWCA | 33 | | 1 | | |
| LCQSLG**F**TYPGWLAGWCA | 34 | | 1 | | |
| LCQSLGVTYPGWLAGWC**S** | 35 | | 1 | | |
| LCQSLGVTYPGWL**V**GWCA | 36 | | 1 | | |
| LCQSL**A**VTYPGWLAGWCA | 37 | | 1 | | |
| LCQSLGV**R**YPGWLAGWCA | 38 | | 2 | | |
| LCQSLGV**L**YPGWLAGWCA | 39 | | 1 | | |
| LCQSLG**P**TYPGWLAGWCA | 40 | | 2 | | |
| **M**CQSLGVTYPGWLAGWCA | 41 | | 1 | | |
| LCQSLG**LR**YPGWLAGWCA | 42 | | 1 | | |
| LCQSLGVTYPGWLAGWC**G** | 43 | | 1 | | |

Fig. 15a

| | | | |
|---|---|---|---|
| LCQ**R**LGVT**W**PGWLAGWCA | 44 | 2 | 2 |
| LCQSLG**ATW**PGWLAGWCA | 45 | 1 | |
| LCQ**R**LGV**SW**PGWLAGWCA | 46 | 2 | 1 |
| LCQSL**P**V**R**YPGWL**S**GWC**S** | 47 | 1 | |
| LCQ**R**LGV**GW**PGWLAGWCA | 48 | 3 | 5 |
| LCQ**N**LG**I**T**W**PGWLAGWCA | 49 | 1 | |
| LCQSLGVT**F**PGWLAGWCA | 50 | 1 | |
| LCQSLG**DK**YPGWLAGWCA | 51 | 1 | 3 |
| LCQSLGV**GW**PGWLAGWCA | 52 | 1 | 3 |
| LCQ**R**LGVT**W**PGWL**T**GWCA | 53 | 1 | |
| LCQSLGVTYPGWL**T**GWCA | 54 | 1 | |
| LCQSLG**A**TYPGWL**W**GWCA | 55 | 1 | |
| LCQSLG**D**TYPGWLAGWCA | 56 | 1 | |
| LCQSLGV**G**YPGWLAGWCA | 57 | 1 | 2 |
| LCQSLGVT**W**PGWLAGWCA | 58 | 3 | 4 |

Fig. 15b

| | | |
|---|---|---|
| LCQ**R**LGVTYPGWLAGWCA | 59 | 1 |
| LCQ**R**LG**A**T**W**PGWLAGWCA | 60 | 2 |
| LCQSLGV**NW**PGWLAGWCA | 61 | 1 |
| LCQSLGV**SW**PGWL**T**GWCA | 62 | 1 |
| LCQ**R**LG**IGW**PGWLAGWCA | 63 | 1 |
| LCQ**R**LGV**GW**PGW**V**AGWCA | 64 | 1 |
| LCQSLGV**S**YPGWL**T**GWCA | 65 | 1 |
| LCQ**H**LGVT**W**PGWLAGWCA | 66 | 1 |
| LCQSLG**IG**YPGWL**T**GWCA | 67 | 1 |
| LCQ**R**L**V**V**GW**PGWLAGWCA | 68 | 1 |
| LCQ**R**LGVT**W**PGW**I**AGWCA | 69 | 1 |
| LCQS**WQ**VT**W**PGWLAGWCA | 70 | 2 |
| LCQ**R**L**EA**T**W**PGWL**V**GWCA | 71 | 1 |
| LCQSLGV**GW**PGWL**T**GWCA | 72 | 1 |
| LCQSLGV**N**YPGWLAGWCA | 73 | 1 |
| LCQ**RF**GV**GF**PGWLAGWCA | 74 | 1 |
| LCQ**N**LGVT**W**PGWLAGWCA | 75 | 1 |
| LCQ**R**LGV**GW**PGWL**S**GWCA | 76 | 1 |
| LCQ**R**LGVT**W**PGWL**W**GWCA | 77 | 1 |
| LCQSL**R**V**RQ**PGWL**S**GWCA | 78 | 1 |

Fig. 15c

SEQUENCE LISTING

<160> NUMBER OF SEQ ID NOS: 81

<210> SEQ ID NO 1
<211> LENGTH: 79
<212> TYPE: DNA
<213> ORGANISM: Artificial Sequence
<220> FEATURE:
<223> OTHER INFORMATION: H5 oligonucleotide

<400> SEQUENCE: 1

```
ctacaaagac ctgtgtcaga gtttgggggt tacgtatccg ggttggttgg cggggtggtg     60

tgcggcggcc gcagtgtga                                                  79
```

<210> SEQ ID NO 2
<211> LENGTH: 44
<212> TYPE: PRT
<213> ORGANISM: Artificial Sequence
<220> FEATURE:
<223> OTHER INFORMATION: clone 13 peptide

<400> SEQUENCE: 2

```
Asp Tyr Lys Asp Ala Gln Trp Trp Thr Thr Ile Gly Ser Asn Met Phe
  1               5                  10                  15

Val Leu Pro Gly Leu Arg Gly Cys Thr Phe Leu Pro Pro Met Gln Cys
             20                  25                  30

Asp Arg Glu Ile Arg Val Phe Leu Val Val Val His
         35                  40
```

<210> SEQ ID NO 3
<211> LENGTH: 44
<212> TYPE: PRT
<213> ORGANISM: Artificial Sequence
<220> FEATURE:
<223> OTHER INFORMATION: clone hh peptide

<400> SEQUENCE: 3

```
Asp Tyr Lys Asp Ala Leu Leu His Arg Ser Arg Cys Val Arg Trp Gly
  1               5                  10                  15

Lys Trp Val Cys Cys Leu Pro Pro Val Gly Val Gly Gly Ala Gln Ala
             20                  25                  30

Asn Gln Gly Met Ser Val Gln Arg Phe Arg His Cys
         35                  40
```

<210> SEQ ID NO 4
<211> LENGTH: 16
<212> TYPE: PRT
<213> ORGANISM: Artificial Sequence
<220> FEATURE:
<223> OTHER INFORMATION: consensus sequence, wherein X1 is S, R, T, N, H, or A; X2 is L, W, or F; X3 is G, A, V, P, Q, E, or R; X4 is V, I, A, L, D, E, P, or F; X5 is T, G, S, R, K, N, A, L, or W; X6 is Y, W, F, or Q;
<220> FEATURE:
<223> OTHER INFORMATION: X7 is L, V, or I; X8 is A, T, S, V, W, or D; X9 is G, A, S, or R

<400> SEQUENCE: 4

```
Cys Gln Xaa Xaa Xaa Xaa Xaa Xaa Pro Gly Trp Xaa Xaa Xaa Trp Cys
  1               5                  10                  15
```

<210> SEQ ID NO 5
<211> LENGTH: 20
<212> TYPE: PRT

-continued

<213> ORGANISM: Artificial Sequence
<220> FEATURE:
<223> OTHER INFORMATION: #445 peptide derivative

<400> SEQUENCE: 5

Leu Cys Gln Arg Leu Gly Val Gly Trp Pro Gly Trp Leu Ser Gly Trp
1 5 10 15

Cys Ala Lys Lys
20

<210> SEQ ID NO 6
<211> LENGTH: 20
<212> TYPE: PRT
<213> ORGANISM: Artificial Sequence
<220> FEATURE:
<223> OTHER INFORMATION: #418 peptide derivative

<400> SEQUENCE: 6

Leu Cys Gln Ser Trp Gln Val Thr Trp Pro Gly Trp Leu Ala Gly Trp
1 5 10 15

Cys Ala Lys Lys
20

<210> SEQ ID NO 7
<211> LENGTH: 40
<212> TYPE: PRT
<213> ORGANISM: Artificial Sequence
<220> FEATURE:
<223> OTHER INFORMATION: clone 13 peptide derivative

<400> SEQUENCE: 7

Ala Gln Trp Trp Thr Thr Ile Gly Ser Asn Met Phe Val Leu Pro Gly
1 5 10 15

Leu Arg Gly Cys Thr Phe Leu Pro Pro Met Gln Cys Asp Arg Glu Ile
20 25 30

Arg Val Phe Leu Val Val Val His
35 40

<210> SEQ ID NO 8
<211> LENGTH: 22
<212> TYPE: PRT
<213> ORGANISM: Artificial Sequence
<220> FEATURE:
<223> OTHER INFORMATION: H5 peptide

<400> SEQUENCE: 8

Asp Tyr Lys Asp Leu Cys Gln Ser Leu Gly Val Thr Tyr Pro Gly Trp
1 5 10 15

Leu Ala Gly Trp Cys Ala
20

<210> SEQ ID NO 9
<211> LENGTH: 14
<212> TYPE: PRT
<213> ORGANISM: Artificial Sequence
<220> FEATURE:
<223> OTHER INFORMATION: H10 peptide

<400> SEQUENCE: 9

Trp Leu Gly Cys Tyr Phe Val Ala Gly Val Val Ala Cys Val
1 5 10

<210> SEQ ID NO 10
<211> LENGTH: 22

-continued

```
<212> TYPE: PRT
<213> ORGANISM: Artificial Sequence
<220> FEATURE:
<223> OTHER INFORMATION: control peptide

<400> SEQUENCE: 10

Asp Tyr Lys Asp Trp Cys Leu Thr Leu Gln Pro Leu Val Trp Ala Ser
  1               5                  10                  15

Gly Gly Gly Tyr Cys Ala
             20


<210> SEQ ID NO 11
<211> LENGTH: 22
<212> TYPE: PRT
<213> ORGANISM: Artificial Sequence
<220> FEATURE:
<223> OTHER INFORMATION: #447 peptide

<400> SEQUENCE: 11

Asp Tyr Lys Asp Leu Cys Gln Arg Leu Gly Val Gly Trp Pro Gly Trp
  1               5                  10                  15

Leu Ser Gly Trp Cys Ala
             20


<210> SEQ ID NO 12
<211> LENGTH: 22
<212> TYPE: PRT
<213> ORGANISM: Artificial Sequence
<220> FEATURE:
<223> OTHER INFORMATION: #418 peptide

<400> SEQUENCE: 12

Asp Tyr Lys Asp Leu Cys Gln Ser Trp Gln Val Thr Trp Pro Gly Trp
  1               5                  10                  15

Leu Ala Gly Trp Cys Ala
             20


<210> SEQ ID NO 13
<211> LENGTH: 22
<212> TYPE: PRT
<213> ORGANISM: Artificial Sequence
<220> FEATURE:
<223> OTHER INFORMATION: #445 peptide

<400> SEQUENCE: 13

Asp Tyr Lys Asp Leu Cys Gln Arg Leu Gly Val Gly Trp Pro Gly Trp
  1               5                  10                  15

Leu Ala Gly Trp Cys Ala
             20


<210> SEQ ID NO 14
<211> LENGTH: 22
<212> TYPE: PRT
<213> ORGANISM: Artificial Sequence
<220> FEATURE:
<223> OTHER INFORMATION: #443 peptide

<400> SEQUENCE: 14

Asp Tyr Lys Asp Leu Cys Gln Arg Leu Gly Val Thr Trp Pro Gly Trp
  1               5                  10                  15

Leu Ala Gly Trp Cys Ala
             20


<210> SEQ ID NO 15
```

-continued

<211> LENGTH: 19
<212> TYPE: PRT
<213> ORGANISM: Artificial Sequence
<220> FEATURE:
<223> OTHER INFORMATION: hydrophilic tail of rGHBP construct

<400> SEQUENCE: 15

Glu Glu Gly Pro Lys Phe Asn Ser Gln His Pro His Gln Glu Ile Asp
1 5 10 15

Asn His Leu

<210> SEQ ID NO 16
<211> LENGTH: 18
<212> TYPE: PRT
<213> ORGANISM: Artificial Sequence
<220> FEATURE:
<223> OTHER INFORMATION: H5 peptide secondary library starting sequence

<400> SEQUENCE: 16

Leu Cys Gln Ser Leu Gly Val Thr Tyr Pro Gly Trp Leu Ala Gly Trp
1 5 10 15

Cys Ala

<210> SEQ ID NO 17
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 17

Leu Cys Gln Ser Leu Gly Ile Thr Tyr Pro Gly Trp Leu Ala Gly Trp
1 5 10 15

Cys Ala

<210> SEQ ID NO 18
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 18

Leu Cys Gln Thr Leu Gly Val Thr Tyr Pro Gly Trp Leu Ala Gly Trp
1 5 10 15

Cys Ala

<210> SEQ ID NO 19
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 19

Leu Cys Gln Ser Leu Gly Val Lys Tyr Pro Gly Trp Leu Ala Gly Trp
1 5 10 15

Cys Ala

<210> SEQ ID NO 20
<211> LENGTH: 18
<212> TYPE: PRT
<213> ORGANISM: Artificial Sequence
<220> FEATURE:

-continued

<223> OTHER INFORMATION: H5 peptide secondary library sequence

<400> SEQUENCE: 20

Leu Cys Gln Ser Leu Gly Val Lys Tyr Pro Gly Trp Leu Thr Gly Trp
1 5 10 15

Cys Ala

<210> SEQ ID NO 21
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 21

Leu Cys Gln Ser Leu Gly Val Thr Tyr Pro Gly Trp Leu Ser Gly Trp
1 5 10 15

Cys Ala

<210> SEQ ID NO 22
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 22

Leu Cys Gln Ser Leu Gly Val Ala Tyr Pro Gly Trp Leu Ala Gly Trp
1 5 10 15

Cys Ala

<210> SEQ ID NO 23
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 23

Leu Cys Gln Ser Leu Gly Val Thr Phe Pro Gly Trp Leu Ser Gly Trp
1 5 10 15

Cys Ala

<210> SEQ ID NO 24
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 24

Leu Cys Gln Ala Leu Gly Val Thr Tyr Pro Gly Trp Leu Ala Gly Trp
1 5 10 15

Cys Ala

<210> SEQ ID NO 25
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 25

-continued

```
Leu Cys Gln Ser Leu Gly Val Ser Tyr Pro Gly Trp Leu Ala Gly Trp
  1               5                  10                  15

Cys Ala


<210> SEQ ID NO 26
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 26

Leu Cys Gln Ser Leu Gly Val Thr Tyr Pro Gly Trp Leu Ala Ala Trp
  1               5                  10                  15

Cys Arg


<210> SEQ ID NO 27
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 27

Leu Cys Gln Ser Leu Gly Val Thr Tyr Pro Gly Trp Leu Asp Gly Trp
  1               5                  10                  15

Cys Ala


<210> SEQ ID NO 28
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 28

Leu Cys Gln Ser Leu Gly Val Ser Tyr Pro Gly Trp Leu Val Gly Trp
  1               5                  10                  15

Cys Ala


<210> SEQ ID NO 29
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 29

Leu Cys Gln Thr Leu Gly Val Lys Tyr Pro Gly Trp Leu Ala Gly Trp
  1               5                  10                  15

Cys Ala


<210> SEQ ID NO 30
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 30

Leu Cys Gln Ser Leu Gly Leu Thr Tyr Pro Gly Trp Leu Ala Gly Trp
  1               5                  10                  15

Cys Gly
```

-continued

<210> SEQ ID NO 31
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 31

Leu Cys Gln Ser Leu Gly Glu Ala Tyr Pro Gly Trp Leu Ala Gly Trp
1 5 10 15

Cys Ala

<210> SEQ ID NO 32
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 32

Leu Cys Gln Arg Leu Gly Leu Thr Trp Pro Gly Trp Leu Ala Gly Trp
1 5 10 15

Cys Ala

<210> SEQ ID NO 33
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 33

Leu Cys Gln Ser Leu Gly Val Trp Trp Pro Gly Trp Leu Ala Gly Trp
1 5 10 15

Cys Ala

<210> SEQ ID NO 34
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 34

Leu Cys Gln Ser Leu Gly Phe Thr Tyr Pro Gly Trp Leu Ala Gly Trp
1 5 10 15

Cys Ala

<210> SEQ ID NO 35
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 35

Leu Cys Gln Ser Leu Gly Val Thr Tyr Pro Gly Trp Leu Ala Gly Trp
1 5 10 15

Cys Ser

<210> SEQ ID NO 36
<211> LENGTH: 18

-continued

<212> TYPE: PRT
<213> ORGANISM: Artificial Sequence
<220> FEATURE:
<223> OTHER INFORMATION: H5 peptide secondary library sequence

<400> SEQUENCE: 36

Leu Cys Gln Ser Leu Gly Val Thr Tyr Pro Gly Trp Leu Val Gly Trp
1 5 10 15

Cys Ala

<210> SEQ ID NO 37
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 37

Leu Cys Gln Ser Leu Ala Val Thr Tyr Pro Gly Trp Leu Ala Gly Trp
1 5 10 15

Cys Ala

<210> SEQ ID NO 38
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 38

Leu Cys Gln Ser Leu Gly Val Arg Tyr Pro Gly Trp Leu Ala Gly Trp
1 5 10 15

Cys Ala

<210> SEQ ID NO 39
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 39

Leu Cys Gln Ser Leu Gly Val Leu Tyr Pro Gly Trp Leu Ala Gly Trp
1 5 10 15

Cys Ala

<210> SEQ ID NO 40
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 40

Leu Cys Gln Ser Leu Gly Pro Thr Tyr Pro Gly Trp Leu Ala Gly Trp
1 5 10 15

Cys Ala

<210> SEQ ID NO 41
<211> LENGTH: 18
<212> TYPE: PRT
<213> ORGANISM: Artificial Sequence
<220> FEATURE:
<223> OTHER INFORMATION: H5 peptide secondary library sequence -continued

<400> SEQUENCE: 41

Met Cys Gln Ser Leu Gly Val Thr Tyr Pro Gly Trp Leu Ala Gly Trp
1 5 10 15

Cys Ala

<210> SEQ ID NO 42
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 42

Leu Cys Gln Ser Leu Gly Leu Arg Tyr Pro Gly Trp Leu Ala Gly Trp
1 5 10 15

Cys Ala

<210> SEQ ID NO 43
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 43

Leu Cys Gln Ser Leu Gly Val Thr Tyr Pro Gly Trp Leu Ala Gly Trp
1 5 10 15

Cys Gly

<210> SEQ ID NO 44
<211> LENGTH: 18
<212> TYPE: PRT
<213> ORGANISM: Artificial Sequence
<220> FEATURE:
<223> OTHER INFORMATION: H5 peptide secondary library sequence #443

<400> SEQUENCE: 44

Leu Cys Gln Arg Leu Gly Val Thr Trp Pro Gly Trp Leu Ala Gly Trp
1 5 10 15

Cys Ala

<210> SEQ ID NO 45
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 45

Leu Cys Gln Ser Leu Gly Ala Thr Trp Pro Gly Trp Leu Ala Gly Trp
1 5 10 15

Cys Ala

<210> SEQ ID NO 46
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 46

Leu Cys Gln Arg Leu Gly Val Ser Trp Pro Gly Trp Leu Ala Gly Trp

-continued

```
  1               5                   10                  15

Cys Ala


<210> SEQ ID NO 47
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 47

Leu Cys Gln Ser Leu Pro Val Arg Tyr Pro Gly Trp Leu Ser Gly Trp
  1               5                   10                  15

Cys Ser


<210> SEQ ID NO 48
<211> LENGTH: 18
<212> TYPE: PRT
<213> ORGANISM: Artificial Sequence
<220> FEATURE:
<223> OTHER INFORMATION: H5 peptide secondary library sequence H5-445

<400> SEQUENCE: 48

Leu Cys Gln Arg Leu Gly Val Gly Trp Pro Gly Trp Leu Ala Gly Trp
  1               5                   10                  15

Cys Ala


<210> SEQ ID NO 49
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 49

Leu Cys Gln Asn Leu Gly Ile Thr Trp Pro Gly Trp Leu Ala Gly Trp
  1               5                   10                  15

Cys Ala


<210> SEQ ID NO 50
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 50

Leu Cys Gln Ser Leu Gly Val Thr Phe Pro Gly Trp Leu Ala Gly Trp
  1               5                   10                  15

Cys Ala


<210> SEQ ID NO 51
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 51

Leu Cys Gln Ser Leu Gly Asp Lys Tyr Pro Gly Trp Leu Ala Gly Trp
  1               5                   10                  15

Cys Ala
```

-continued

<210> SEQ ID NO 52
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 52

Leu Cys Gln Ser Leu Gly Val Gly Trp Pro Gly Trp Leu Ala Gly Trp
1 5 10 15

Cys Ala

<210> SEQ ID NO 53
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 53

Leu Cys Gln Arg Leu Gly Val Thr Trp Pro Gly Trp Leu Thr Gly Trp
1 5 10 15

Cys Ala

<210> SEQ ID NO 54
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 54

Leu Cys Gln Ser Leu Gly Val Thr Tyr Pro Gly Trp Leu Thr Gly Trp
1 5 10 15

Cys Ala

<210> SEQ ID NO 55
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 55

Leu Cys Gln Ser Leu Gly Ala Thr Tyr Pro Gly Trp Leu Trp Gly Trp
1 5 10 15

Cys Ala

<210> SEQ ID NO 56
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 56

Leu Cys Gln Ser Leu Gly Asp Thr Tyr Pro Gly Trp Leu Ala Gly Trp
1 5 10 15

Cys Ala

<210> SEQ ID NO 57
<211> LENGTH: 18
<212> TYPE: PRT

-continued

<213> ORGANISM: Artificial Sequence
<220> FEATURE:
<223> OTHER INFORMATION: H5 peptide secondary library sequence

<400> SEQUENCE: 57

Leu Cys Gln Ser Leu Gly Val Gly Tyr Pro Gly Trp Leu Ala Gly Trp
1 5 10 15

Cys Ala

<210> SEQ ID NO 58
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 58

Leu Cys Gln Ser Leu Gly Val Thr Trp Pro Gly Trp Leu Ala Gly Trp
1 5 10 15

Cys Ala

<210> SEQ ID NO 59
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 59

Leu Cys Gln Arg Leu Gly Val Thr Tyr Pro Gly Trp Leu Ala Gly Trp
1 5 10 15

Cys Ala

<210> SEQ ID NO 60
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 60

Leu Cys Gln Arg Leu Gly Ala Thr Trp Pro Gly Trp Leu Ala Gly Trp
1 5 10 15

Cys Ala

<210> SEQ ID NO 61
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 61

Leu Cys Gln Ser Leu Gly Val Asn Trp Pro Gly Trp Leu Ala Gly Trp
1 5 10 15

Cys Ala

<210> SEQ ID NO 62
<211> LENGTH: 18
<212> TYPE: PRT
<213> ORGANISM: Artificial Sequence
<220> FEATURE:
<223> OTHER INFORMATION: H5 peptide secondary library sequence -continued

<400> SEQUENCE: 62

Leu Cys Gln Ser Leu Gly Val Ser Trp Pro Gly Trp Leu Thr Gly Trp
1 5 10 15

Cys Ala

<210> SEQ ID NO 63
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 63

Leu Cys Gln Arg Leu Gly Ile Gly Trp Pro Gly Trp Leu Ala Gly Trp
1 5 10 15

Cys Ala

<210> SEQ ID NO 64
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 64

Leu Cys Gln Arg Leu Gly Val Gly Trp Pro Gly Trp Val Ala Gly Trp
1 5 10 15

Cys Ala

<210> SEQ ID NO 65
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 65

Leu Cys Gln Ser Leu Gly Val Ser Tyr Pro Gly Trp Leu Thr Gly Trp
1 5 10 15

Cys Ala

<210> SEQ ID NO 66
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 66

Leu Cys Gln His Leu Gly Val Thr Trp Pro Gly Trp Leu Ala Gly Trp
1 5 10 15

Cys Ala

<210> SEQ ID NO 67
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 67

Leu Cys Gln Ser Leu Gly Ile Gly Tyr Pro Gly Trp Leu Thr Gly Trp
1 5 10 15

-continued

Cys Ala

<210> SEQ ID NO 68
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 68

Leu Cys Gln Arg Leu Val Val Gly Trp Pro Gly Trp Leu Ala Gly Trp
1 5 10 15

Cys Ala

<210> SEQ ID NO 69
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 69

Leu Cys Gln Arg Leu Gly Val Thr Trp Pro Gly Trp Ile Ala Gly Trp
1 5 10 15

Cys Ala

<210> SEQ ID NO 70
<211> LENGTH: 18
<212> TYPE: PRT
<213> ORGANISM: Artificial Sequence
<220> FEATURE:
<223> OTHER INFORMATION: H5 peptide secondary library sequence #418

<400> SEQUENCE: 70

Leu Cys Gln Ser Trp Gln Val Thr Trp Pro Gly Trp Leu Ala Gly Trp
1 5 10 15

Cys Ala

<210> SEQ ID NO 71
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 71

Leu Cys Gln Arg Leu Glu Ala Thr Trp Pro Gly Trp Leu Val Gly Trp
1 5 10 15

Cys Ala

<210> SEQ ID NO 72
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 72

Leu Cys Gln Ser Leu Gly Val Gly Trp Pro Gly Trp Leu Thr Gly Trp
1 5 10 15

Cys Ala

-continued

<210> SEQ ID NO 73
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 73

```
Leu Cys Gln Ser Leu Gly Val Asn Tyr Pro Gly Trp Leu Ala Gly Trp
  1               5                  10                  15

Cys Ala
```

<210> SEQ ID NO 74
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 74

```
Leu Cys Gln Arg Phe Gly Val Gly Phe Pro Gly Trp Leu Ala Gly Trp
  1               5                  10                  15

Cys Ala
```

<210> SEQ ID NO 75
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 75

```
Leu Cys Gln Asn Leu Gly Val Thr Trp Pro Gly Trp Leu Ala Gly Trp
  1               5                  10                  15

Cys Ala
```

<210> SEQ ID NO 76
<211> LENGTH: 18
<212> TYPE: PRT
<213> ORGANISM: Artificial Sequence
<220> FEATURE:
<223> OTHER INFORMATION: H5 peptide secondary library sequence #447

<400> SEQUENCE: 76

```
Leu Cys Gln Arg Leu Gly Val Gly Trp Pro Gly Trp Leu Ser Gly Trp
  1               5                  10                  15

Cys Ala
```

<210> SEQ ID NO 77
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 77

```
Leu Cys Gln Arg Leu Gly Val Thr Trp Pro Gly Trp Leu Trp Gly Trp
  1               5                  10                  15

Cys Ala
```

<210> SEQ ID NO 78
<211> LENGTH: 18
<212> TYPE: PRT
<213> ORGANISM: Artificial Sequence -continued

```
<220> FEATURE:
<223> OTHER INFORMATION: H5 peptide secondary library sequence

<400> SEQUENCE: 78

Leu Cys Gln Ser Leu Arg Val Arg Gln Pro Gly Trp Leu Ser Gly Trp
  1               5                  10                  15

Cys Ala


<210> SEQ ID NO 79
<211> LENGTH: 4
<212> TYPE: PRT
<213> ORGANISM: Artificial Sequence
<220> FEATURE:
<223> OTHER INFORMATION: Flag-tag sequence

<400> SEQUENCE: 79

Asp Tyr Lys Asp
  1


<210> SEQ ID NO 80
<211> LENGTH: 6
<212> TYPE: PRT
<213> ORGANISM: Artificial Sequence
<220> FEATURE:
<223> OTHER INFORMATION: H10 peptide

<400> SEQUENCE: 80

Asp Tyr Lys Asp Phe Pro
  1               5


<210> SEQ ID NO 81
<211> LENGTH: 20
<212> TYPE: PRT
<213> ORGANISM: Artificial Sequence
<220> FEATURE:
<223> OTHER INFORMATION: H10 peptide

<400> SEQUENCE: 81

Val Cys Trp Arg Ala His Phe Arg Ser Leu Gly Leu Glu Ser Ser Phe
  1               5                  10                  15

Ala Gly Gly Gly
            20
```

COMPOUNDS THAT BIND GROWTH TO HORMONE RECEPTOR

BACKGROUND AND SUMMARY OF THE INVENTION

Growth hormone (GH), also referred to as somatotropin, plays an important role in animal growth and development. It regulates a variety of physiological effects, including linear growth of the animal, lactation, differentiation and electrolyte balance. The molecular mechanism of these biological effects involves the binding of gowth hormone to a specific plasma membrane receptor, referred to as growth hormone receptor (GHR).

Growth hormones from different species share a significant level of sequence homology. Human GH (huGH) is a polypeptide chain of 190 amino acids (aa) and a molecular weight of 22 kDa, while rat GH is 189aa long and has 64% sequence homology to its human counterpart. Growth hormone binds to a GHR, which consists of three domains: an extracellular hormone-binding domain, which is 28 kDa for the human GHR, a single pass transmembrane domain and an intracellular domain, which is 35 ka for the human GHR. A soluble form of the extracellular domain occurs naturally in blood as a growth hormone binding protein (GHBP). The molecular interactions between GH and membrane-bound GHR are thought to be analogous to those between GH and soluble GHBP. Receptor activation requires simultaneous binding of two GHR by one GH, i.e., receptor dimerization, to form a complex wherein the two intracellular domains can initiate the process of signal transduction underlying GH activity.

Rat GHBP (rGHBP), like its membrane bound form (rGHR), is fully cross-reactive with both human and rat GH (rGH). The human GHR, and human GHBP, can bind only the human GH (huGH) and not the rGH.

The ability to control the activation of GHR is important in developing new therapies for certain diseases such as dwarfism and acromegaly. Recombinant huGH is presently on the market as a drug for dwarfism. Injectable formulations of bovine GH also are used in animal husbandry to promote growth and milk production in cows.

Although proteins have become highly visible as potential drugs, their use as therapeutics presents several difficult problems, including the high cost of production and formulation, administration via injection and limited stability in the bloodstream. Therefore, replacing proteins, including GH, with a small molecular weight drug has received a lot of attention. However, none of these efforts has resulted in finding a successful drug. A key problem to replacing GH, as with some other proteins, is that a small molecule that binds to one receptor site would only be an antagonist. A dimer of two small molecules, capable of binding to two receptor units and dimerizing them, is needed for agonist activity. Up to now there is no assay for such dimers.

The present invention is focused on finding peptides that specifically recognize the sites involved in activation of proteins of pharmacological importance. Once identified and characterized as regulators of target activity, these peptides may be used in high throughput screens to identify and provide information on small molecules which bind at these sites and, when dimerized, mimic the function of GH.

Yanofsky et al. (PNAS 93:7391–7386) describes the isolation of a monomer peptide antagonistic to IL-1 with nanomolar affinity for the IL-1 receptor. This effort required construction and use of many phage-display peptide libraries and sophisticated phage panning procedures.

Wrighton et al. (Science, 278:458–463) and Livnah et al. (Science, 273: 469–471) reported dimer peptides that bind to the erythropoietin (EPO) receptor with fall agonistic activity in vivo. These peptides are cyclical and have intra-peptide disulfide bonds; like the IL-1 receptor antagonist, they show no significant sequence identity to the natural ligand. Importantly, X-ray crystallography revealed that it was the spontaneous formation of non-covalent homodimers that enabled it to dimerize two EPO receptors.

Most recently Cwirla et al. (Science, 276:1696–1699) described the identification of two families of peptides that bind to the human thrombopoietin (TPO) receptor and are competed by the binding of the natural ligand TPO. The one with highest affinity, when dimerized by chemical means proved to be as potent an in vivo agonist as TPO.

The present invention provides assays for identifying compounds that mimic the binding characteristics of growth hormone. Such compounds would serve as antagonists of growth hormone function. Dimers of such compounds would serve as growth hormone agonists.

The present invention also provides polypeptides that inhibit binding of growth hormone to growth hormone receptor. Such polypeptides are used in the assays of the invention to identify compounds that mimic growth hormone.

BRIEF DESCRIPTION OF THE FIGURES

FIG. 11A shows binding of bGH to rGHBP.

FIG. 11B shows binding of bP#418 (SEQ ID NO:12) to rGHBP.

FIG. 11C shows binding of bP#447 (SEQ ID NO:11) to rGHBP.

FIG. 12A shows competition of bGH (2 nM) with GH.

FIG. 12B shows competition of bGH (2 nM) with Mab2c3.

FIG. 12C shows competition of bP#418 (SEQ ID NO:12; 300 nM) with GH.

FIG. 12D shows competition of bP#418 (SEQ ID NO:12; 300 nM) with Mab2c3.

FIG. 12E shows competition of bP#447 (SEQ ID NO:11; 300 nM) with GH.

FIG. 12F shows competition of bP#447 (SEQ ID NO:11; 300 nM) with Mab2c3.

FIGS. 15A–C show the sequence of peptides from the secondary H5 library that bound to GHBP.

FIG. 15A shows the peptides corresponding to SEQ ID NO.:16–43. bound to GHBP.

FIG. 15B shows the peptides corresponding to SEQ ID NO.: 44–58.

FIG. 15C shows the peptides corresponding to SEQ ID NO.: 59–78.

DETAILED DESCRIPTION OF THE INVENTION

Figure 1:
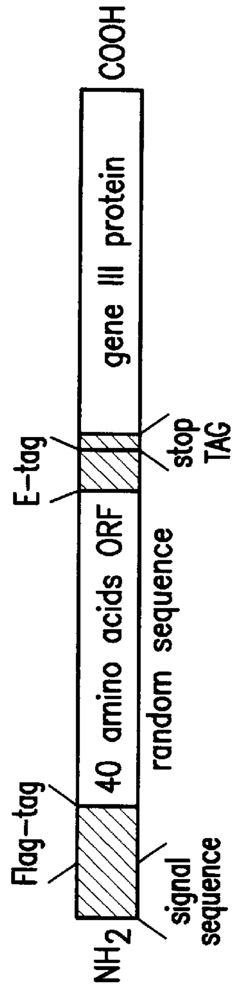
FIG. 1 shows a schematic diagram for the peptide library.

Assays have been developed for the purpose of identifying compounds that bind to and dimerize two growth hormone receptor subunits. Such compounds would mimic the function of growth hormone, and would thus be useful as therapeutic agents. The assays are based on the discovery and identification of peptides that bind to a growth hormone receptor subunit (GHBP) and inhibit the binding of growth hormone to growth hormone receptor.

Randomly generated nucleic acid sequences were used to generate libraries of phage capable of expressing random peptides encoded by the nucleic acid sequences. The phage-displayed peptides were screened for binding to rGHBP and phage which express peptides that bind rGHBP were obtained. Certain peptides were determined to be capable of competitive inhibition of binding of growth hormone to rG1BP. These peptides thus mimic the binding characteristics of growth hormone, and can be used in assays to identify other compounds that inhibit the binding of the peptides to rGHBP.

The designing of mimetics to a known pharmaceutically active compound is a known approach to the development of pharmaceuticals based on a "lead" compound. This might be desirable where the active compound is difficult or expensive to synthesize or where it is unsuitable for a particular method of administration, e.g. peptides are unsuitable active agents for oral compositions as they tend to be quickly degraded by proteases in the alimentary canal. Mimetic design, synthesis and testing is generally used to avoid randomly screening large number of molecules for a target property.

There are several steps commonly taken in the design of a mimetic from a compound having a given target property. Firstly, the particular parts of the compound that are critical and/or important in determining the target property are determined. In the case of a peptide, this can be done by systematically varying the amino acid residues in the peptide, e.g. by substituting each residue in turn. These parts or residues constituting the active region of the compound are known as its "pharmacophore".

Once the pharmacophore has been found, its structure is modeled according to its physical properties, e.g.

stereochemistry, bonding, size and/or charge, using data from a range of sources, e.g. spectroscopic techniques, X-ray diffraction data and NMR. Computational analysis, similarity mapping (which models the charge and/or volume of a pharmacophore, rather than the bonding between atoms) and other techniques can be used in this modeling process.

In a variant of this approach, the three dimensional structure of the ligand and its binding partner are modeled. This can be especially useful where the ligand and/or binding partner change conformation on binding, allowing the model to take account of this in the design of the mimetic.

A template molecule is then selected onto which chemical groups that mimic the pharmacophore can be grafted. The template molecule and the chemical groups grafted on to it can conveniently be selected so that the mimetic is easy to synthesis, is likely to be pharmacologically acceptable, and does not degrade in vivo, while retaining the biological activity of the lead compound. The mimetic or mimetics found by this approach can then be screened to see whether they have the target property, or to what extent they exhibit it. Further optimization or modification can then be carried out to arrive at one or more final mimetics for in vivo or clinical testing.

In order to identify compounds that are useful in the above-described methods, compounds may be screened for interference of the growth hormone/growth hormone receptor interaction. Suitable screening methods would be based upon observations with regard to compounds that interfere with the binding between peptides that comprise or represent the binding site of a receptor. Such methods include, but are not limited to, immunoassay techniques such as radioimmunoassay (RIA), enzyme linked immunoadsorbent assay (ELISA), and radioligand binding assays which are well known in the art.

Peptides that bind to rGHBP have been identified.

The peptides of the present invention are artificial, i.e. non-naturally occurring, peptides or polypeptides. Artificial peptides useful in the invention may be obtained through various means such as chemical synthesis, phage display, cleavage of proteins or polypeptides into fragments, or any means by which polypeptides may be made or obtained.

The assays of the present invention have identified growth hormone receptor binding amino acid sequences. In specific embodiments, the growth hormone receptor binding amino acid sequences comprise the sequence LCQRLGVGWPG-WLSGWCAKK (SEQ ID NO:5); LCQSWQVTWPGW-LAGWCAKK (SEQ ID NO:6); OR AQWWTTIGSNMFV-LPGLRGCTFLPPMQCDREIRVFLVVVH (SEQ ID NO:7), or any of the sequences of SEQ ID NOS: 2, 3, 5–8, 11–14 or 16–78.

We have selected the basic format of an in vitro competitive receptor-binding assay as the basis of a High Throughput Screen (HTS) for small organic molecular replacements for GH. In the present assay, occupation of the active site of rGHBP is quantified by Time Resolved Fluorometric Detection (TRFD) with streptavidin-labeled europium (saEu) complexed to biotinylated peptides (bP). In this assay, saEu forms a ternary complex with bP and rGHBP (i.e., the rGHBP:bP:saEu complex). The TRFD assay format is well established, sensitive, and quantitative (Tompkins et al.). We first demonstrate the assay using biotinylated GH (bGH) as bLigand and then show that biotinylated H5-mutant peptides bP#447 (SEQ ID NO:11) and bP#418 (SEQ ID NO:12) can also be used as bLigand. Furthermore, we show that the assay faithfully reports the competition of ligand binding to the active site of rGHR.

In these assays, soluble rGHBP is attached to the surface of microtiter wells, then incubated with bP. Unbound bP is than washed away and (sa)Eu is added to complex with receptor bound bP. The rGHBP:bP bound (sa)Eu is then converted into its highly fluorescent state and detected by TRFD.

The present invention also provides a method for interfering with the binding between growth hormone and growth hormone receptor which method comprises administering an effective amount of a peptide which is able to disrupt or prevent the binding between growth hormone and growth hormone receptor or a functional peptide analogue thereof.

Also encompassed by the present invention are kits for identifying compounds that bind to growth hormone receptor, comprising growth hormone and a growth hormone receptor binding amino acid sequence. In one embodiment, the kit comprises growth hormone receptor and a growth hormone receptor binding amino acid sequence as separate constituents.

EXAMPLE 1

Construction of Phage Library

DNA fragments coding for peptides containing 40 random amino acids were generated in the following manner. A 145 base oligonucleotide was synthesized to contain the sequence $(NNK)_{40}$, where N=A, C, T, or G, and K=G or T. This oligonucleotide was used as the template in a PCR amplification along with two shorter oligo primers, both of which were biotinylated at their 5' ends. The resulting 190 bp product was purified and concentrated with QIAquick spin columns (Qiagen), then digested with Sfi I and Not I restriction enzymes. Streptavidin-agarose (GIBCO) was added to the digestion mixture to remove the cleaved ends of the PCR product as well as any uncut DNA. The resulting 150 bp fragment was again purified over QIAquick spin columns.

The phagemid pCANTAB5E (Pharmacia) was digested with Sfi I and Not I, followed by phosphatase treatment. The digested DNA was purified using a 1% agarose gel followed by QIAEX II (Qiagen). The vector and insert were ligated overnight at 15° C. The ligation product was purified using QIAquick spin columns (Qiagen) and electroporations were performed at 1500 volts in an electroporation cuvette (0.1 mm gap; 0.5 ml volume) containing 12.5 μg of DNA and 500 μg of TG1 electrocompetent cells. Immediately after the pulse, 12.5 ml of pre-warmed (40° C.) 2xYT medium containing 2% glucose (2xYT-G) was added and the transformants were grown at 37° C. for one hour. Cell transformants were pooled, the volume measured, and an aliquot was plated onto 2xYT-G containing 100 μg/ml ampicillin (2xYT-AG) plates to determine the total number of transformants. Sequence analysis of randomly selected clones indicated that 54% of all clones are in-frame (Mandecki et al., 1997).

Preparation of Electrocompetent Cells

To prepare electrocompetent cells an overnight culture of *E. coli* TG1 cells (F'traD36 $lacI^q$ Δ(lacZ)M15 proA+B+/supE Δ(hsdM-mcrB)5 $r_k$-$m_k$-McrB-) thi Δ(lac-proAB) was diluted to an $O.D._{600}$=0.05–0.1 in 500 ml 2xYT, then grown at 37° C. in 4 liter Ehrlenmyer flasks to an $O.D._{600}$=0.5–0.6. The culture was poured into pre-chilled centrifuge bottles and incubated on ice for 30 minutes prior to centrifugation at 2000×g for 30 minutes (2° C.). The supernatant was poured off, and the cell pellet was resuspended in a total of 400 ml of ice cold sterile distilled water. The process of centrifugation and resuspension was repeated two more times. After the last centrifugation, the pellet was resuspended in a total of 25 ml of ice cold water containing 10% glycerol. The cell suspension was transferred to pre-chilled 35 ml centrifuge bottles, and was then pelleted at 2000×g for 10 minutes at 4° C. The cells were then suspended in 0.3 ml of the same 10% glycerol solution, aliquoted into smaller tubes, and snap-frozen on dry ice. The aliquots were stored at −80° C.

To amplify the library, the transformants were inoculated into four liters of 2xYT-AG medium and allowed to grow until the $A_{600}$ increased approximately 400 times. The cells were pelleted by centrifugation at 3000×g for 20 minutes, then resuspended in 40 ml 2xYT-AG to which glycerol was added to a final concentration of 8%. The library was stored at −80° C.

This process was carried out using the standard phage preparation protocol (above) with the following changes. Five individual recombinant cell libraries, with a total diversity of $1.6\times10^{10}$, were combined and grown to O.D.$_{600}$=0.5 in 2xYT-AG at 30° C. with shaking (250 RPM). Helper phage (M13K07) was then added (MOI=15), and the cells were incubated for 30 minutes at 37° C. without shaking, followed by 30 minutes at 37° C. with shaking (250 RPM). The precipitated phage pellet was resuspended in phosphate-buffered saline (1/100 of the initial culture volume) and passed through a 0.45 μm filter. The phage were titered by infecting TG1 cells. The phage titer was $4\times10^{13}$ cfu/ml.

To prepare the phage, bacterial cells containing phagemid were grown to O.D.$_{600}$=0.5 in 2xYT-AG [yeast tryptone medium containing 100 mg/ml ampicillin and 2% glucose] at 37° C. with shaking (250 RPM). M13K07 helper phage was then added (MOI [multiplicity of infection]=15), and the cells were incubated for 30 minutes at 37° C. with gentle shaking. Following infection, cells were pelleted and the supernatant containing the helper phage was discarded. The cell pellet was resuspended in the initial culture volume of 2xYT-A (no glucose) containing 50 mg/ml kanamycin and grown overnight at 30° C. with shaking (250 RPM). The cells from the overnight culture pelleted at 3000×g for 30 minutes at 4° C. and the supernatant containing the phage was recovered. The solution was adjusted to 4% PEG, 500 mM NaCl and chilled on ice for one hour. The precipitated phage were pelleted by centrifugation at 10,000×g for 30 minutes. The pellet was resuspended in PBS containing 2% non-fat dried milk (MPBS).

A standard method was used to coat and block all microtiter plates. The target protein of interest was diluted to 1 mg/ml in 50 mM sodium carbonate buffer, pH 9.5. One hundred microliters of this solution was added to an appropriate number of wells in a 96-well microtiter plate (MaxiSorp plates, Nunc) and incubated overnight at 4° C. Wells were then blocked with MPBS at room temperature for one hour.

EXAMPLE 2

Expression and Purification of Growth Hormone Binding Protein

Construction of the Humanized GHBP

DNA encoding the rat GHBP was used as a template. A total of three PCR reactions were performed. The first of these amplified the DNA encoding amino acids 1–48 of GHBP. The 3' oligo used for this reaction encoded the mutation L43R (CTG→AGA). The second PCR reaction amplified the DNA encoding amino acids 38–260 of GHBP. The 5' oligo used for this reaction was complementary to the 3' oligo used for the first reaction, and also encoded the L43R mutation. Both PCR products were purified using QIAquik spin columns (Qiagen), then mixed in equimolar amounts and reamplified using the 5' oligo from the first reaction and the 3' oligo from the second reaction. This resulting full-length DNA was again purified over a QIAquik spin column, then sequenced to verify the changed sequence. Expression and purification of the humanized GHBP were done essentially as described above.

An overnight culture was diluted 1:100 into 1 liter of 2xYT media containing 100 μug/ml ampicillin. This culture was grown to O.D.$_{600}$=0.6, then induced with 1 mM IPTG for three hours. The cells were pelleted, and the pellet was resuspended in 60 ml of sonication buffer (50 mM Tris-HCl, pH 8.0; 150 mM NaCl; 1 mM PMSF). After sonication, the material was centrifuged at 4000 rpm for 20 minutes at 4° C. The resulting pellet was re-sonicated and centrifuged as above. This pellet was then resuspended in extraction buffer (8M urea; 50 mM Tris-HCl, pH 8.0) and incubated at room temperature for 4 hours with gentle rotation. The material was then centrifuged at 16,000 rpm for 20 minutes, and the resulting supernatant was filtered through a 0.45 μm filter. The 6x-His tagged material was loaded onto a Ni-NTA column previously equilibrated with running buffer (PBS and 8M urea). The column was washed with 10 column volumes of running buffer containing 0.5 mM imidazole. The protein was eluted with running buffer containing 150 mM imidazole. Fractions were dialyzed overnight against PBS containing 0.2 mM PMSF. The dialyzed sample was then clarified by centrifugation at 14,000 rpm for 10 minutes.

EXAMPLE 3

Panning Growth Hormone Binding Protein

The peptide library was panned against soluble rGHBP. The microtiter plates were then coated with MAb 4.3 and then blocked with milk. Mab 4.3 is a non-neutralizing murine IgG specific for the carboxyl terminal tail of GHBP that results from alternative splicing of the mRNA. Soluble rGHBP was added next and after 2 hrs unbound rGHBP was removed by washing, and the standard panning procedure was initiated, with eight wells used for each round of panning. The phage were incubated with MPBS for 30 minutes at room temperature, then 100 μl was added to each well. For the first round, the input phage titer was $4\times10^{13}$ cfu/ml. For rounds 2 and 3, the input phage titer was approximately $10^{11}$ cfu/ml. Phage were allowed to bind for two to three hours at room temperature. The wells were then quickly washed 13 times with 200 μl/well of MPBS. Bound phage were eluted by incubation with 100 μl/well of 20 mM glycine-HCl, pH 2.2 for 30 seconds. The resulting solution was then neutralized with Tris-HCl, pH 8.0. Log phase TG1 cells were infected with the eluted phage, then plated onto two 20 cm×20 cm plates containing 2xYT-AG. The plates were incubated at 30° C. overnight. The next morning, cells were removed by scraping and stored in 10% glycerol at −80° C. For subsequent rounds of affinity enrichment, cells from these frozen stocks were grown and phage were prepared as described above. A total of 72 clones were picked at random from the second and third rounds of panning and screened for binding activity.

EXAMPLE 4

ELISA Analyses of Phage

For analysis of individual clones, colonies were picked and phage prepared as described above. Microtiter wells were coated and blocked as described above. Wells were coated with either rGHBP or a control IgG MAb. Phage resuspended in MPBS were added to duplicate wells (100 $\mu$l/well) and incubated at room temperature for one hour. The phage solution was then removed, and the wells were washed three times with PBS at room temperature. Anti-M13 antibody conjugated to horseradish peroxidase (Pharmacia Biotech) was diluted 1:3000 in MPBS and added to each well (100 $\mu$l/well). Incubation was for another hour at room temperature, followed by PBS washes as described. Color was developed by addition of ABTS solution (100 $\mu$l/well; Boebringer). Color development was stopped by adjusting each well to 0.5% SDS. Plates were analyzed at 405 nm using a SpectraMax 340 plate reader (Molecular Devices) and SoftMax Pro software. Data points were averaged after subtraction of appropriate blanks. A clone was considered "positive" if the $A_{405}$ of the well was $\geqq$2-fold over background.

Figure 3:
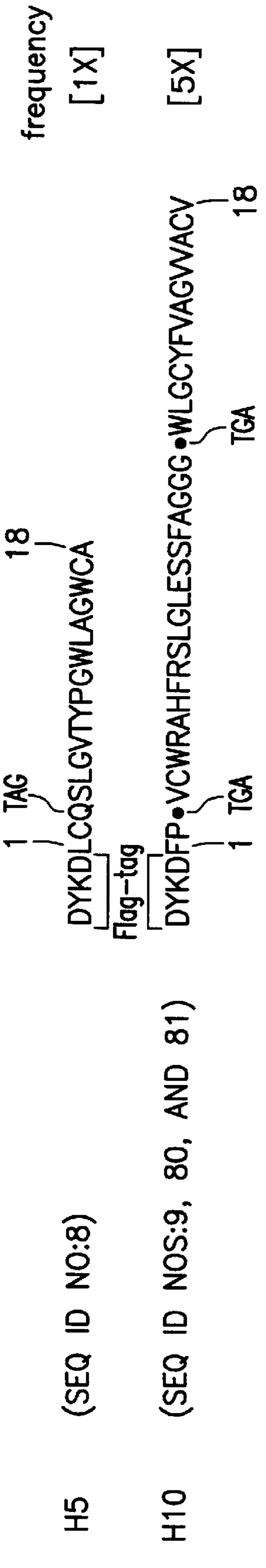
FIG. 3 shows the sequence of H5 (SEQ ID NO:8) and H10 clones (SEQ ID NOS:9, 80, 81). Nonsense codon TAG is suppressed as Q; TGA has no identified suppressor. x=number of times a clone appeared in Round 3 panning (out of 72 total clones).
Figure 2A:
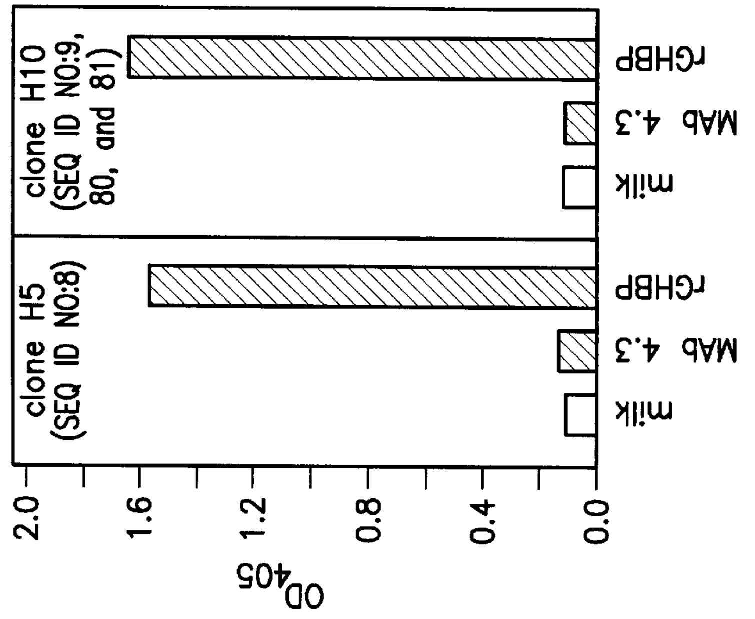
FIG. 2A shows the results of ELISA analysis demonstrating H5 (SEQ ID NO:8) and H10 peptide (SEQ ID NOS:9, 80, 81) mediated phage binding to rGHBP.

Five Round 3 clones were positive as judged by binding to rGHBP (FIG. 2A) and DNA sequence analyses showed that these were comprised of two distinct clones (FIG. 3). The first clone, GHBP-H5 (H5; SEQ ID NO:8), has an open reading frame (ORF) while the other, GHBP-H10 (H10; SEQ ID NOS:9, 80, and 81) does not have an ORF and is referred to as a frame shifted clone.

For $IC_{50}$ determinations in a competitive ELISA, microtiter plates were coated with GHBP and blocked as described. Phage were prepared as described. Prior to addition of phage to plates, H5 peptide (SEQ ID NO:8) or a control peptide (SEQ ID NO:10) was diluted in PBS and added to duplicate wells (100 $\mu$l/well). After incubation for one hour at room temperature, the prepared phage were added to each well (100 $\mu$l/well) without removing the peptide solution. After incubation for another hour at room temperature, the wells were washed and the color developed as described above.

Figure 2B:
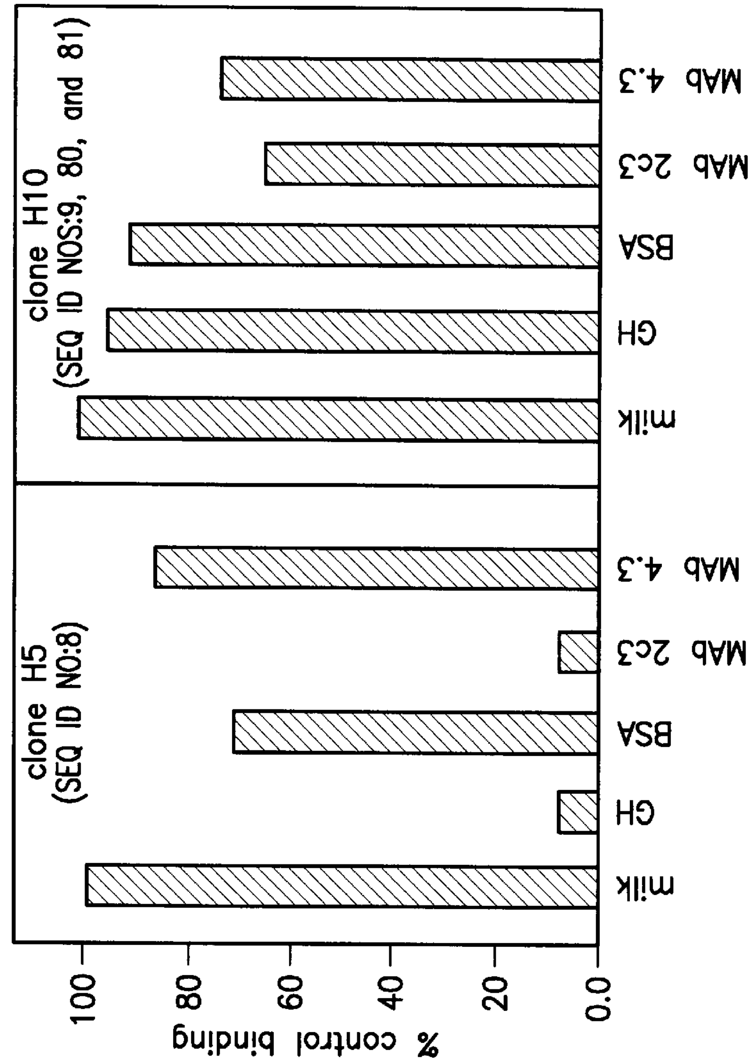
FIG. 2B shows the results of ELISA analysis demonstrating competition of H5 (SEQ ID NO:8) and H10 peptide (SEQ ID NOS:9, 80, 81) mediated phage binding to rGHBP.

These clones were next analyzed for binding to the receptor's active sites (FIG. 2B). Competitions of phage binding were done both with the cognate ligand (i.e., GH) and with a specific target-neutralizing MAb 2C3 (Wang, B. S., et al. Mol. Cellular Endocrinology, vol. 116, p. 223–226, 1996). The binding of H5 (SEQ ID NO:8) was blocked both by GH and by MAb 2C3. The second positive rGHBP clone, H10 (SEQ ID NOS:9, 80, and 81), a shifted clone, was not blocked by either GH or MAb 2C3 (FIG. 2B).

To determine the rank order for phage peptides, the rGHBP (25 $\mu$g/ml) was immobilized onto a CM-5 (BIAcore) sensor chip using amino coupling chemistry and the manufacturer's recommended protocol. The final surface density was 1000 RU. A monoclonal antibody was immobilized onto another flow cell as a control surface. Phage were directly injected (30–100 $\mu$l) with a buffer flow rate of 1 $\mu$l/minute. Background binding to the control surface was subtracted prior to further analysis.

EXAMPLE 5

Secondary Phage Library Based on Clone H5 (SEQ ID NO:8)

Figure 4A:
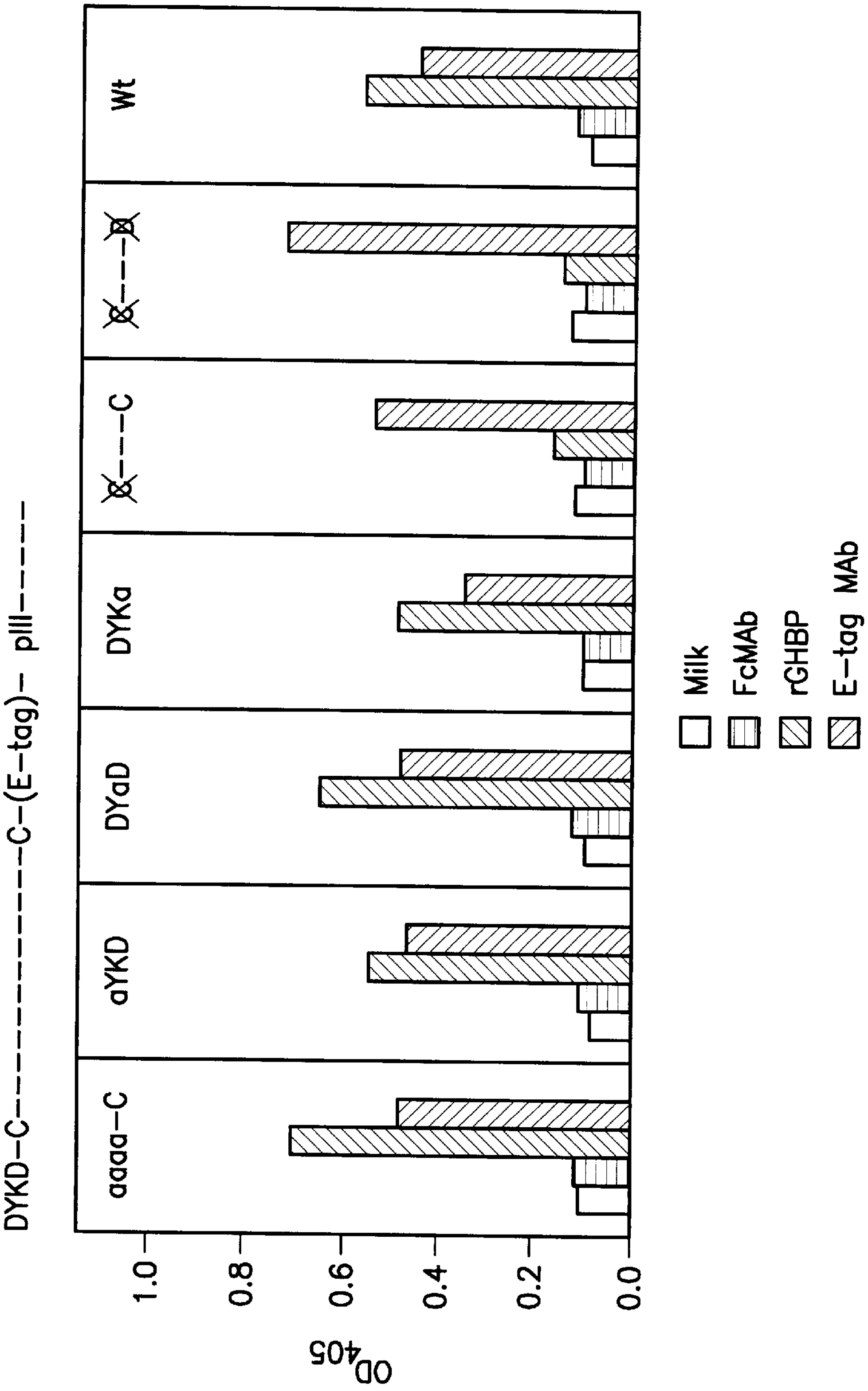
FIG. 4 shows the results of analysis to determine the requirement for the FLAG (DYKD) sequence (SEQ ID NO:79) and cysteine residues for H5 (SEQ ID NO:8) binding to rGHBP.
Figure 4B:
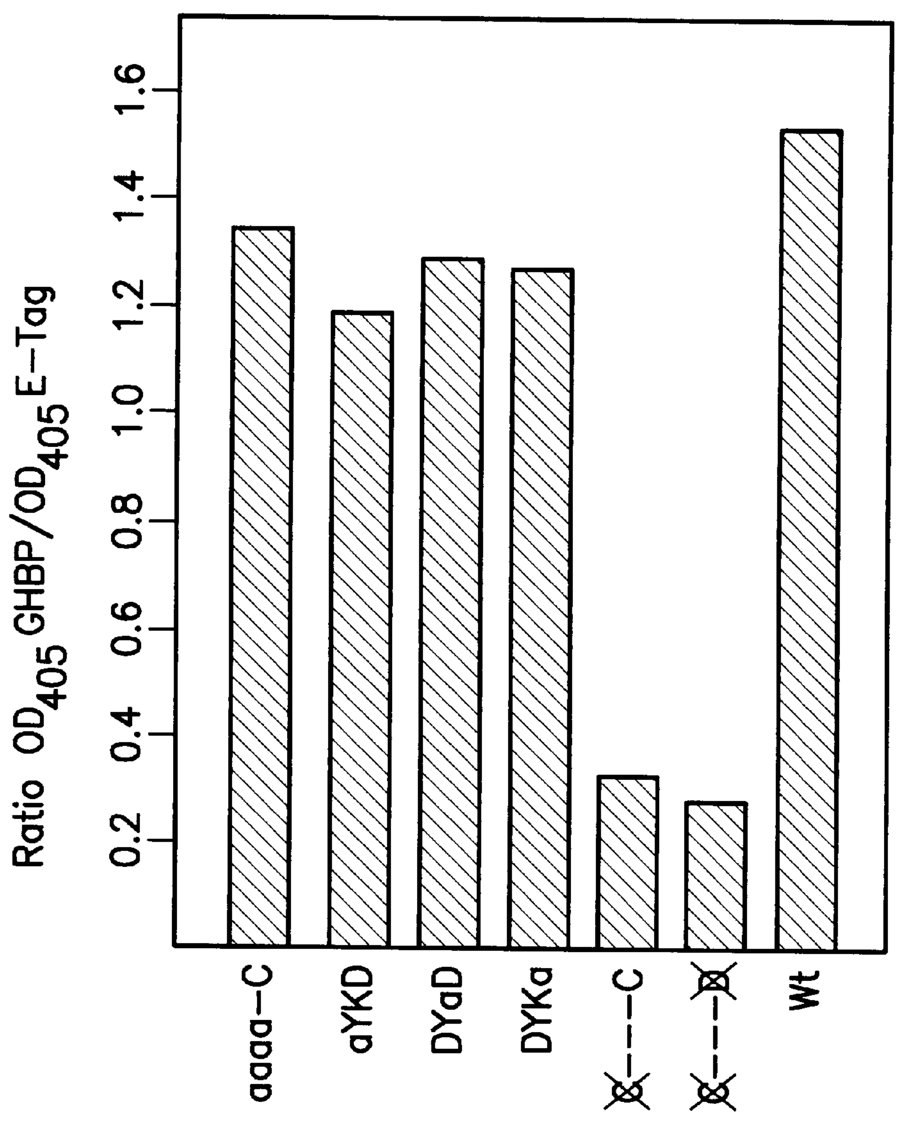

Once the H5 peptide (herein referred to as wild type; H5WT; SEQ ID NO:8) was determined to bind the active site of rGHBP, the peptide's properties were modified using mutagenesis. The goal was to bring the affinity into a range that would allow the peptide to be used in a receptor binding assay and tested in a cell based assay for activity. Before selecting residues for mutagenesis, it was determined that DYKD (SEQ ID NO:79) does not play any role in binding but that both cysteines are essential. In FIG. 4 Alanine replacement for single or multiple amino acid is represented by "a" and for cysteine by "X". Phage were input at $10^{10}$/well. Wild type (WT) and mutant phage were tested on wells coated with milk (2%), FcMAb (100 ng/well), rGHBP (100 ng/well), or MAb specific for the Etag epitope (100 ng/well) (FIG. 4A). Detection with 1RP-anti M13 phage antibody was done as described. The ratio of phage binding to rGHBP vs anti-Etag mAb coated wells with H5 mutants is shown in FIG. 4B. The DYKD (SEQ ID NO:79) residues were therefore not important. Among several available mutagenesis methods, we chose one based on gene synthesis and phage display. In this method a library of doped oligonucleotides carrying several mutations in any single DNA molecule is used to obtain a pool of mutant genes that are phage displayed. This method allowed the encoding of both the original H5WT peptide (SEQ ID NO:8) as control as well as versions containing high numbers of mutations per peptide in a very large library (>$10^{10}$).

Figure 6:
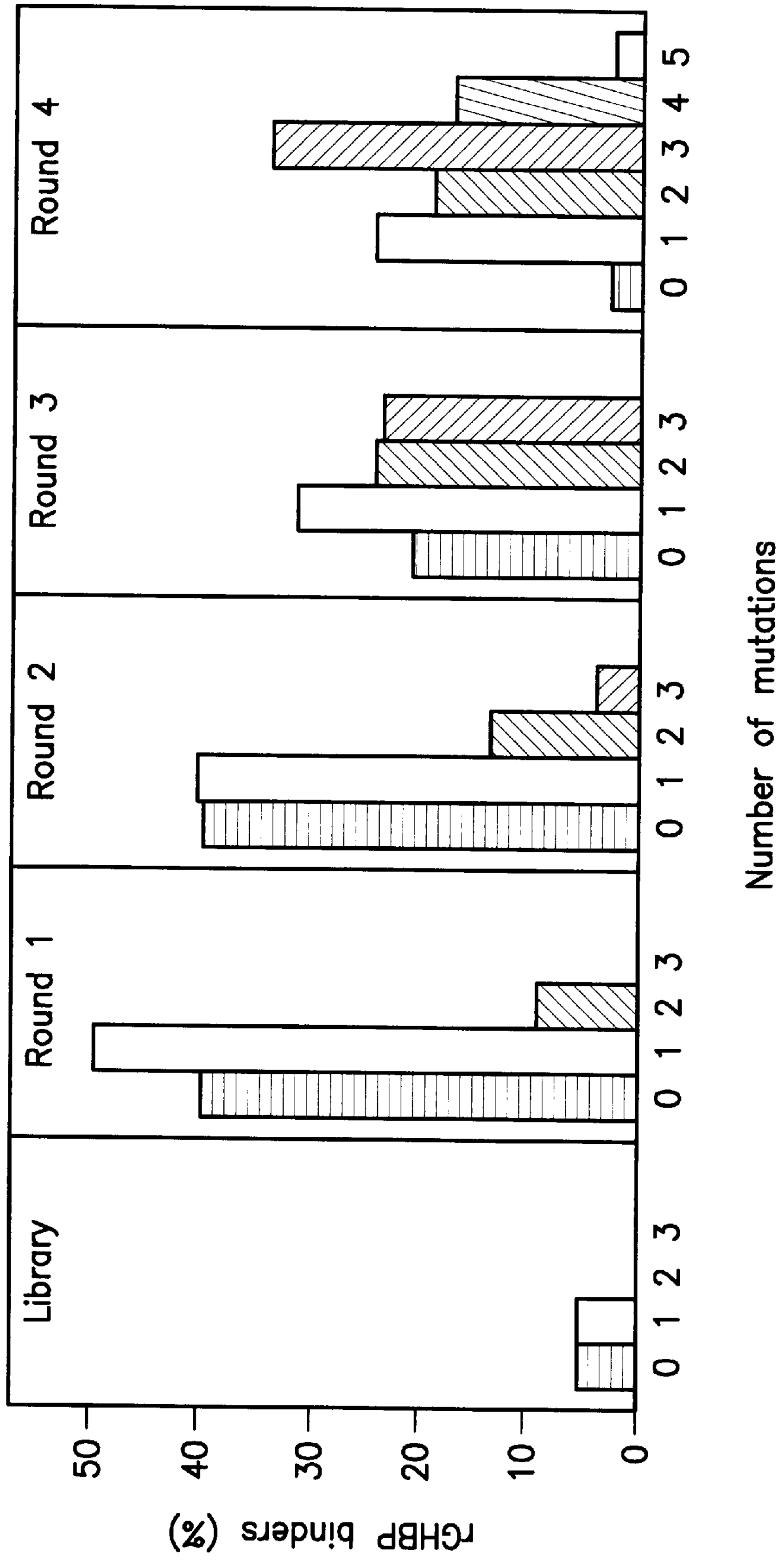
FIG. 6 shows the distribution of the number of amino acid mutations in peptides that bind rGHBP from the secondary H5 library

Therefore H5 secondary mutant library was designed to contain an average of four mutations per peptide. The number of possible mutant H5 peptide sequences having four mutations is $1.0\times10^{10}$ and is equivalent to the actual size of the secondary phage library. Sequence analysis indicates that of these peptides 30% have 3–4, 33% have 1–2 and 32% have 5–6 mutations. There also was a small percent with 7–8 mutations and the H5WT sequence (SEQ ID NO:8) occurs about 5% (FIG. 6, Round 0).

An oligonucleotide based on the DNA sequence encoding the H5WT peptide (SEQ ID NO:8) was synthesized. The sequence of the oligonucleotide is: 5 '-CTACAAAGACC-TGTGTTAGAGTTTGGGGGTTACGTATC-CGGGTTGGTTGG CGGGGTGGTGTGCGGCGGCCGCAGTGTGA-3'(SEQ ID NO:1)

The underlined base positions were synthesized as mixtures of four nucleosides as follows:

A=90% A; 3.3% C; 3.3% G; and 3.3% T

C=3.3% C; 90% C; 3.3% G; and 3.3% T

G=3.3% C; 3.3% C; 90% G; and 3.3% T

T=3.3% C; 3.3% C; 3.3% G; and 90% T

Using this oligo as a template, the H5 secondary library was constructed, electroporated, amplified, and rescued essentially as described for the original peptide library. The final diversity of this secondary library was ~$10^{10}$.

More than 50 randomly picked clones from the secondary library (Round 0, before panning) were rescued and the phage was assayed in an ELISA for binding to the anti-Etag MAb, as well as for binding to the rGHBP (binding to anti-Etag mAb is used as an indicator of expression of displayed peptides on phage surfaces). The results (FIG. 6) show that although most of the clones display a peptide, i.e., are positive for anti-Etag mAb, only about 1% bind to rGHBP. This indicates that the most common outcome of random mutagenesis is the loss of rGHBP affinity. Nevertheless, some mutants had retained their binding properties and some have improved affinities (see below).

EXAMPLE 6

Panning with the Secondary H5 Library

Approximately 100 clones from each round of panning were analyzed in a phage ELISA to identify the clones that bind to the receptor. The positive clones were subjected to DNA sequencing and protein sequence comparison. FIGS. 15A–C provide a listing of different sequences obtained from each round of panning. Data on the right are the number of individual clones found to bind to rGHBP which were isolated from Round 1–4 of panning. Total clones analyzed in round 1–4 respectively were 21, 38, 28 and 40.

Wells were coated with rGHBP (100 ng/well) and blocked as described. FIG. 6 shows the frequency of mutations found among positive binding in each of the panning rounds. The results show clearly that binders from later rounds of panning contain more mutations than do those from earlier rounds. Some binders are present in multiple copies. This is most striking in the results of round 4.

Certain mutations occurred frequently in the rGHBP binders. The residues highly permissible to change among binders are S4-L5-G6-V7-T8-Y9, as well as A14. Rarer mutations were also observed at L1 and I3, G15 and A18. As expected, the two cysteine residues, C2 and 17, were absolutely conserved. The two residues just internal to the two C residues, Q3 and W16, and the triplet P10-G11-W12 were also absolutely conserved. Three point mutations stand out as occurring more than 20 times in the clones sequenced. These are: S4toR T8toG and Y9toW. One of the two clones observed most often (8 times) has these three mutations and no other mutation. The other clone that was observed 8 times has a single point mutation, Y9toW, one of the three mutations seen most frequently. Two other clones were found 5 times each. They carry subsets of the three dominant point mutations, either Y8toG and Y9toW, or S4toR and Y9toW. These data are suggestive of the involvement of the newly mutated residues in binding to the receptor. These results are summarized in FIG. 7, which also gives a consensus rGHBP binding sequence.

Figure 8:
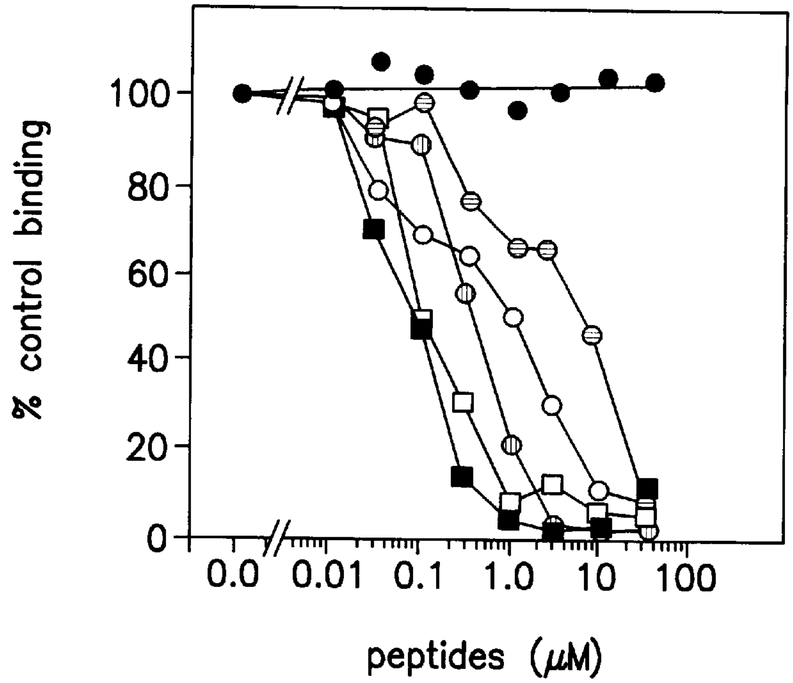
FIG. 8 shows competition of H5 (SEQ ID NO:8) phage binding to rGHBP by synthetic peptides. Wells were coated with rGHBP (100 ng/well) and blocked as described. Peptides were added 1 hr prior to addition of H5 (SEQ ID NO:8) phage ($10^{10}$/well) and incubation continued for 1 hr. Phage binding was detected with HRP-anti M13 phage antibody. Number and sequence of competing peptides are detailed on the right of figure. Control binding=binding in absence of peptide.

The H5WT (SEQ ID NO:8) and a randomly scrambled H5WT control (SEQ ID NO:10) were obtained by chemical synthesis. The mutant phage from different rounds of panning were first compared for affinity for the rGHBP in a competition ELISA in which the $IC_{50}$ of synthetic H5 (SEQ ID NO:8) was determined for each. Based on these results, 12 other peptides were selected for chemical synthesis. All synthetic peptides were then tested as competitors of H5WT (SEQ ID NO:8) phage binding as shown in FIG. 8, and rank ordered as to $IC_{50}$. The highest-ranked sequences most often contain combinations of the most frequently observed point mutations (i.e. S4toR, T8toG and Y9toW). The exception is clone 418 (SEQ ID NO:12) which carries the Y9toW mutation along with two mutations which are not frequently observed (L5toW and G6toE).

A summary of the BIAcore app$K_D$ values are given in Table I and indicate a rank order of potency of GH>>418 (SEQ ID NO:12)=417>443 (SEQ ID NO:14)>H5WT (SEQ ID NO:8). This ranking agrees with phage competition data and the BIAcore analysis done at one concentration in which we observed H5wt (SEQ ID NO:8)>445 (SEQ ID NO:13)=432=436. Clearly the two peptides, #447 (SEQ ID NO:11) and #418 (SEQ ID NO:12), have the highest affinity for rGHBP. Both were selected for development of a high throughput screen (HTS) bioassay.

TABLE I

BIAcore Affinity Measurements of bPeptide binding to rGHBP.

| bPeptide | (app$K_D$ [$\mu$M]) app$K_D$1 | app$K_D$2 |
|---|---|---|
| H5 (SEQ ID NO: 8) | 1.3 | 3.5 |
| #443 (SEQ ID NO: 14) | 0.60 | >10 |
| #447 (SEQ ID NO: 11) | 0.16 | 2.9 |
| #418 (SEQ ID NO: 12) | 0.15 | 0.67 |

Figures 5, 7:
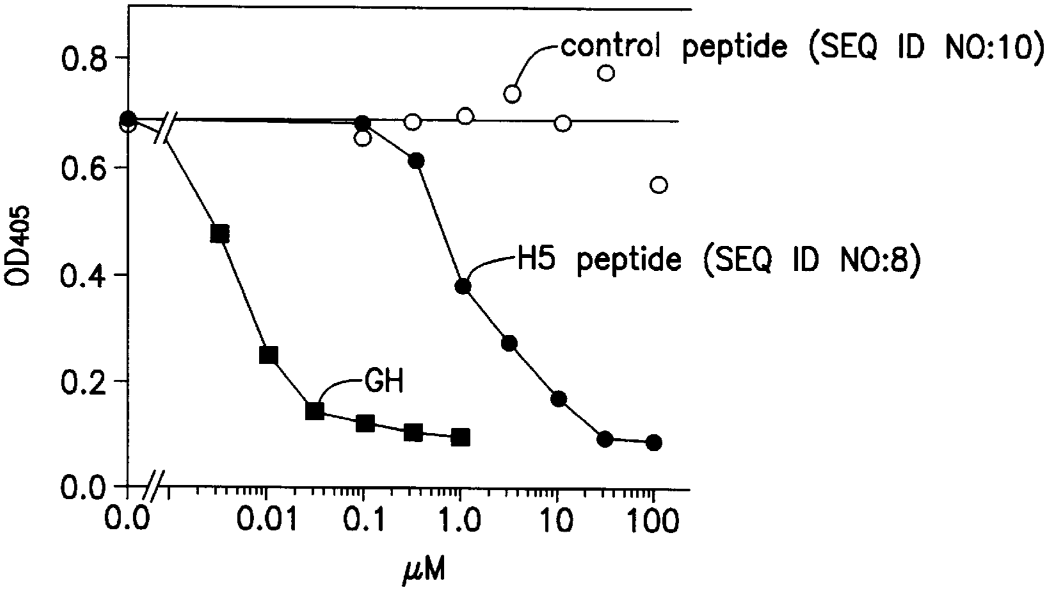
FIG. 5 shows ELISA competition of H5 phage binding to rGHBP by GH, H5 peptide (SEQ ID NO:8) or control peptide (SEQ ID NO:10). Wells were coated with rGHBP (100 ng/well) and blocked as described. Competitor was present prior (1 hr) and during H5 (SEQ ID NO:8) phage incubation (1 hr). Phage was detected with HRP-anti M13 phage antibody and reported at $OD_{405}$ as described. Control peptide (SEQ ID NO:10) contains same amino acids as H5 (SEQ ID NO:8) in randomized order.
FIG. 7 shows the consensus sequence for active site rGHBP binders. H5 sequence (SEQ ID NO:16) is shown in top line. Amino acids found at various positions are identified along with number of times of such appearances among all positive binders. Consensus sequence (SEQ ID NO:63) shows the most frequent amino acid found at each position in active site binders. Amino acids found ≧3 times are indicated below. Positions in bold never changed among all binders.
Figure 9A:
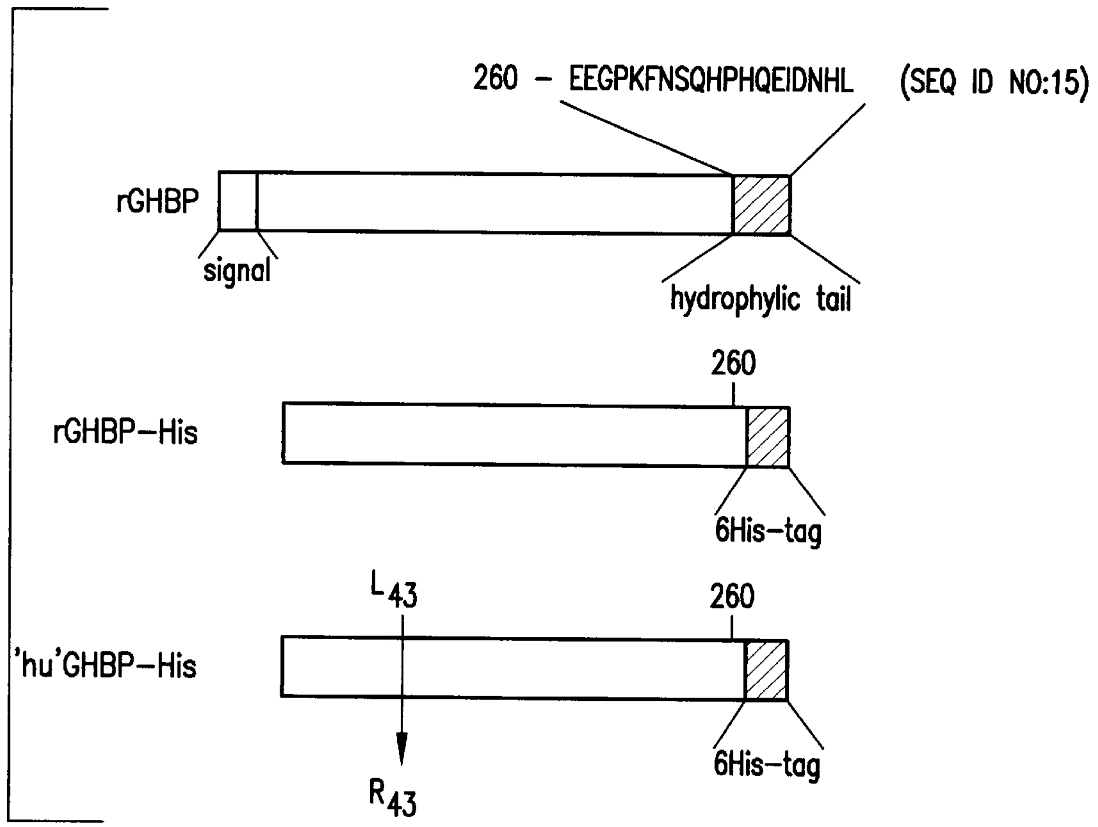
FIG. 9A is a schematic of recombinant expression vectors for rat (r) and 'humanized'('hu') GHBP constructs; tails as shown, 'hu'=humanized by R43 to L43 amino acid change.
Figure 9B:
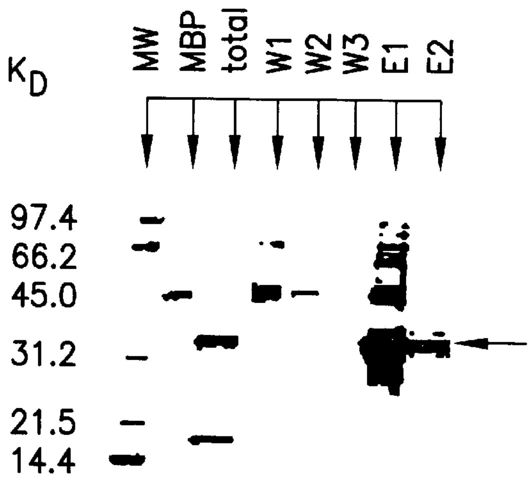
FIG. 9B shows SDS-PAGE analysis of purified rGHBP. MW=molecule weight standards, MBP=maltose binding protein (200 ug); total=total cell extracted, W 1-3=soluble fractions after sonication of inclusion bodies, E1-2=8M urea extractions of inclusion bodies. Kilodaltons are shown in the molecule weights (kD) scale on left. Position of rGHBP (33 kD) is shown by the arrow.
Figure 10A:
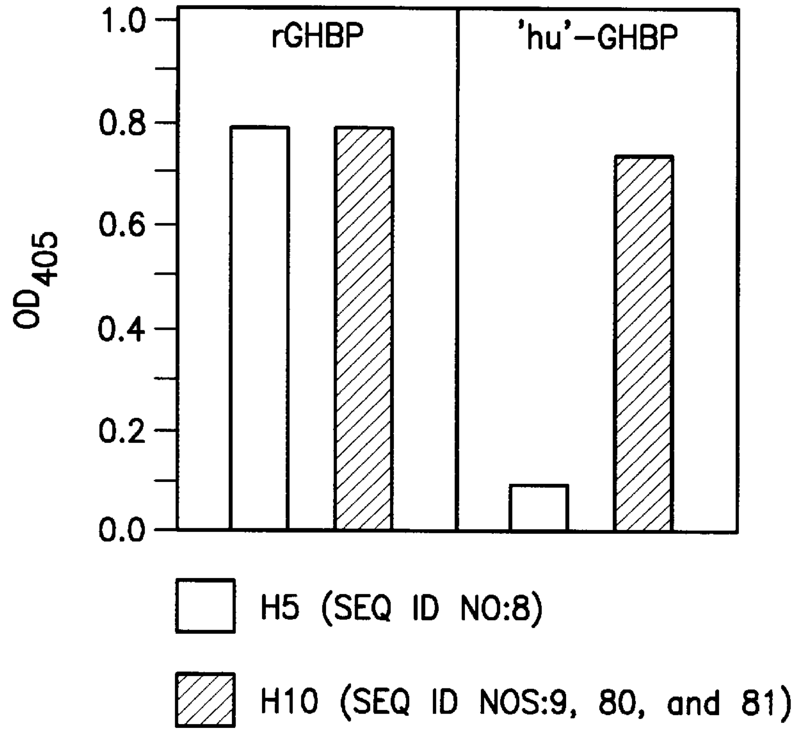
FIG. 10A shows species specificity of H5 (SEQ ID NO:8) binding demonstrated by results from ELISA analysis. Wells were coated with either recombinant rGHBP or 'hu'GHBP (100 ng/well). Additions of H5 (SEQ ID NO:8) and H10 (SEQ ID NOS:9, 80, and 81) phage ($10^{10}$/well) and detection were made as described.
Figure 10B:
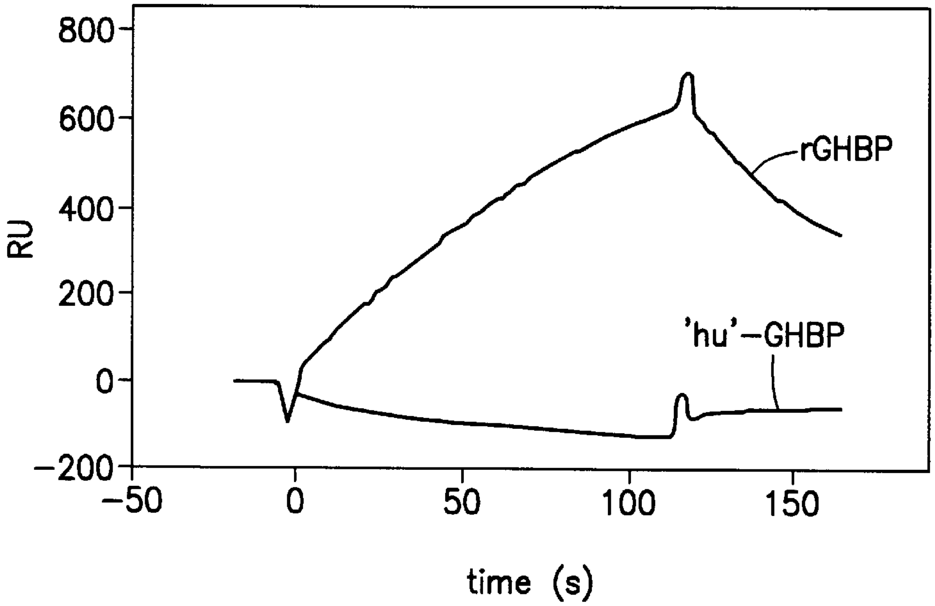
FIG. 10B shows species specificity of H5 (SEQ ID NO:8) binding demonstrated by results from BIAcore analysis. Stepavidin chips were coated with H5 (SEQ ID NO:8) to 1100 RU as described and rGHBP or 'hu'GHBP (500 ug/ml) injected as 30 $\mu$l samples.

Growth hormone receptors from different species bind human GH as well as their own, however the human GH receptor only binds human or monkey GH. Mutational analysis demonstrated that Arg 43 accounts for the species specificity of the human GH receptor Souza, et al., PNAS, vol. 82, p. 959–963, 1995). We altered rGHBP to a "humanized" version ('hu'GHBP) by PCR (FIG. 9A). Partially purified 'hu'GHBP wig. 9B) was tested in binding by ELISA and BIAcore. The 'hu'GHBP binds to human GH but not to bovine GH. H10 peptide (SEQ ID NOS:9, 80, and 81; FIG. 5) binds to rGHBP and 'hu'GHBP, however the H5WT peptide (SEQ ID NO:8), as does rat GH, binds to rGHBP, but not humanized, GHBP (FIG. 10A). BIAcore analysis showed H5WT peptide (SEQ ID NO:8) binds to rGHBP and not the 'hu'GHBP. (FIG. 10B).

EXAMPLE 7

Assays with Synthetic Peptides

Peptide Synthesis

Synthetic peptides were obtained from a commercial supplier (Anaspec). The peptides were supplied greater than 90% pure by HPLC. The molecular weights of the peptides as determined by mass spectroscopy agreed with the expected values.

Equilibrium Binding Constant (KD) Determination

GHBP was immobilized onto one flow-cell of a CM-5 sensor chip (Biosensor) using amine coupling chemistry and the manufacturer's recommended protocol. An unrelated IgG was immobilized in the same manner to another flow cell of the same chip as a control surface. Increasing concentrations of synthetic peptide were injected over both surfaces, and the binding responses were allowed to come to equilibrium. After subtraction of background binding from the control surface, the results were used to derive an equilibrium dissociation constant using Scatchard analysis.

Rank-order Determination of Synthetic Peptides

The rat GHBP (100 $\mu$g/ml) was immobilized onto a CM-5 sensor chip using amino coupling chemistry and the manufacturer's recommended protocol. The final surface density was 4000 RU. A monoclonal antibody was immobilized onto another flow cell as a control surface. Peptides (50 $\mu$g/ml) were injected at a flow rate of 5 $\mu$l/minute. Background binding to the control surface was subtracted prior to further analysis.

Competition of H5 Related Peptide Binding to GHBP

The competition of specific bP#447 (SEQ ID NO:11) and bP#418 (SEQ ID NO:12) binding to the rGHBP was studied in detail using GH (FIG. 12). In these studies, as with those following bGH binding (see FIG. 12A), the competing agents are preincubated with rGHBP before bP addition. The $IC_{50}$ values (FIG. 12B, C and Table II) show that GH competes extremely well with either bP#447 (SEQ ID NO:11) or bP#418 (SEQ ID NO:12) for binding to rGHBP with $IC_{50}$ values of 0.4 and 2 nM, respectively. Maximal competition of total binding by GH is the same for any ligand. From a comparison of $IC_{50}$, GH appears more potent as inhibitors of bP binding than bGH binding. No competition of either peptide is observed with addition of an antibody preparation specific for another protein.

TABLE II

Summary of TRFD Measurements of Specific Ligand binding to GHBP

| | (nM) $ED_{50}$ | $IC_{50}$ (nM) vs. bGH | vs. bP #447 (SEQ ID NO: 11) | vs .bP #418 (SEQ ID NO: 12 |
|---|---|---|---|---|
| bGH | 20 (n = 1) | — | — | — |
| GH | — | 5 (n = 2) | 0.4 (n = 2) | 2 (n = 1) |
| bP #447 (SEQ ID NO: 11) | 600 (n = 6) | — | — | — |
| bP #418 (SEQ ID NO: 12) | 800 (n = 1) | — | — | — |
| DMSO | | >>3% | >>3% | >>3% |

Wells coated with rGHBP (100 ng/well) overnight as described. $ED_{50}$ and $IC_{50}$ calculated from analysis of specific bLigand binding to rGHBP. Competitors added 1 hr prior to addition of bLigand as described.

Specificity of GHBPs

The biotinylated control peptide (SEQ ID NO:10) was immobilized onto one flow cell of a SA-5 (streptavidin coated) sensor chip to a final density of 700 RU. On a second flow cell, either hGH (1100 RU final density), H5WT peptide (SEQ ID NO:8; 1100 RU final density), or bGH (730 RU final density) was immobilized. GHBP (either rat or humanized) was injected at a concentration of 500 μg/ml with a flow rate of 5 μl/minute. Background binding to the control surface was subtracted prior to further analysis.

EXAMPLE 8

Detection of the Binding of Biotinylated GH To GHBP

Figure 11A:
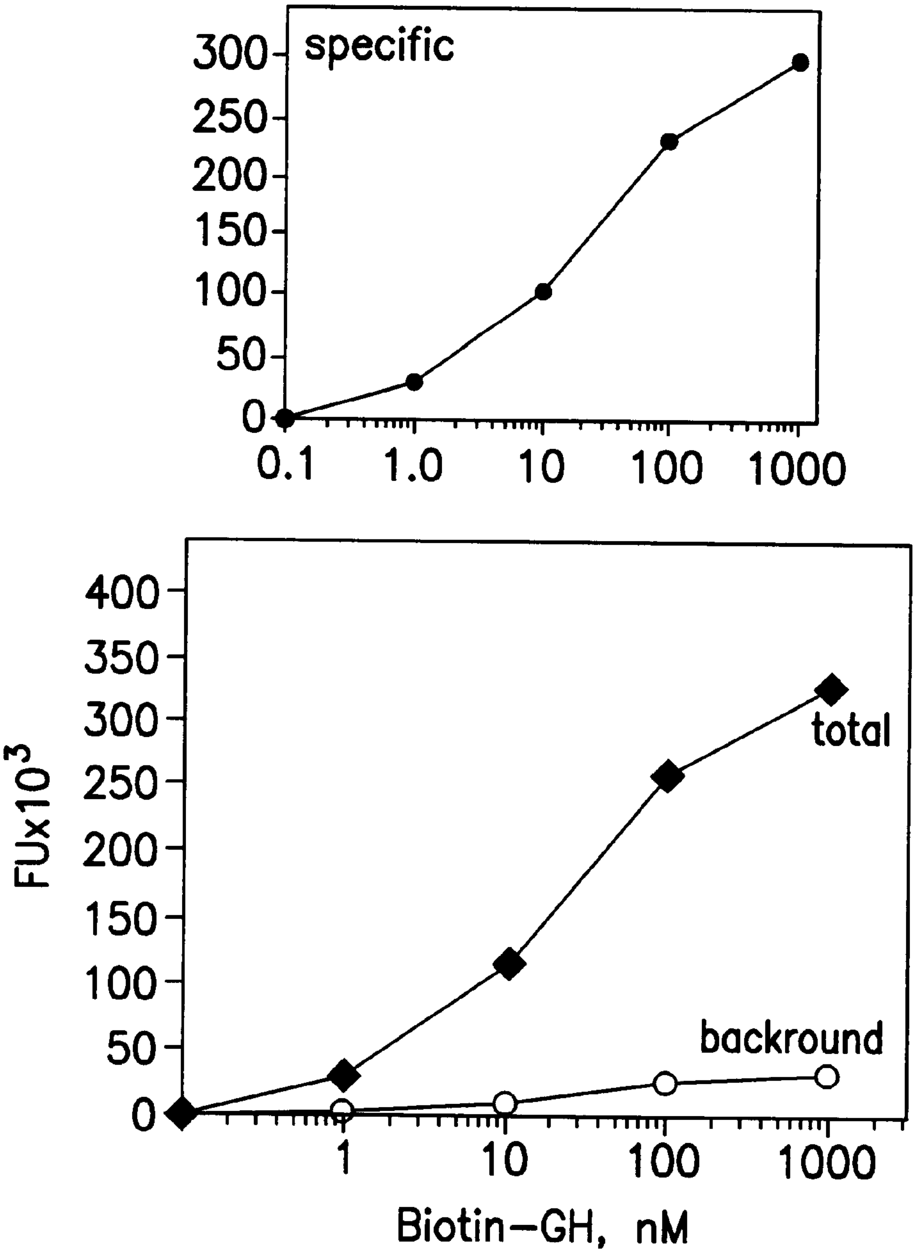
FIGS. 11A–C show binding of bLigands to rGHBP. Wells were coated with rGHBP (100 ng/well) overnight. Increasing concentrations of bLigand were added. Binding was done for 2 hr without (total) or with (background) 1 hr pretreatment with ≧100 excess GH. Insert shows specific binding to rGHBP (i.e., total-background).
Figure 11B:
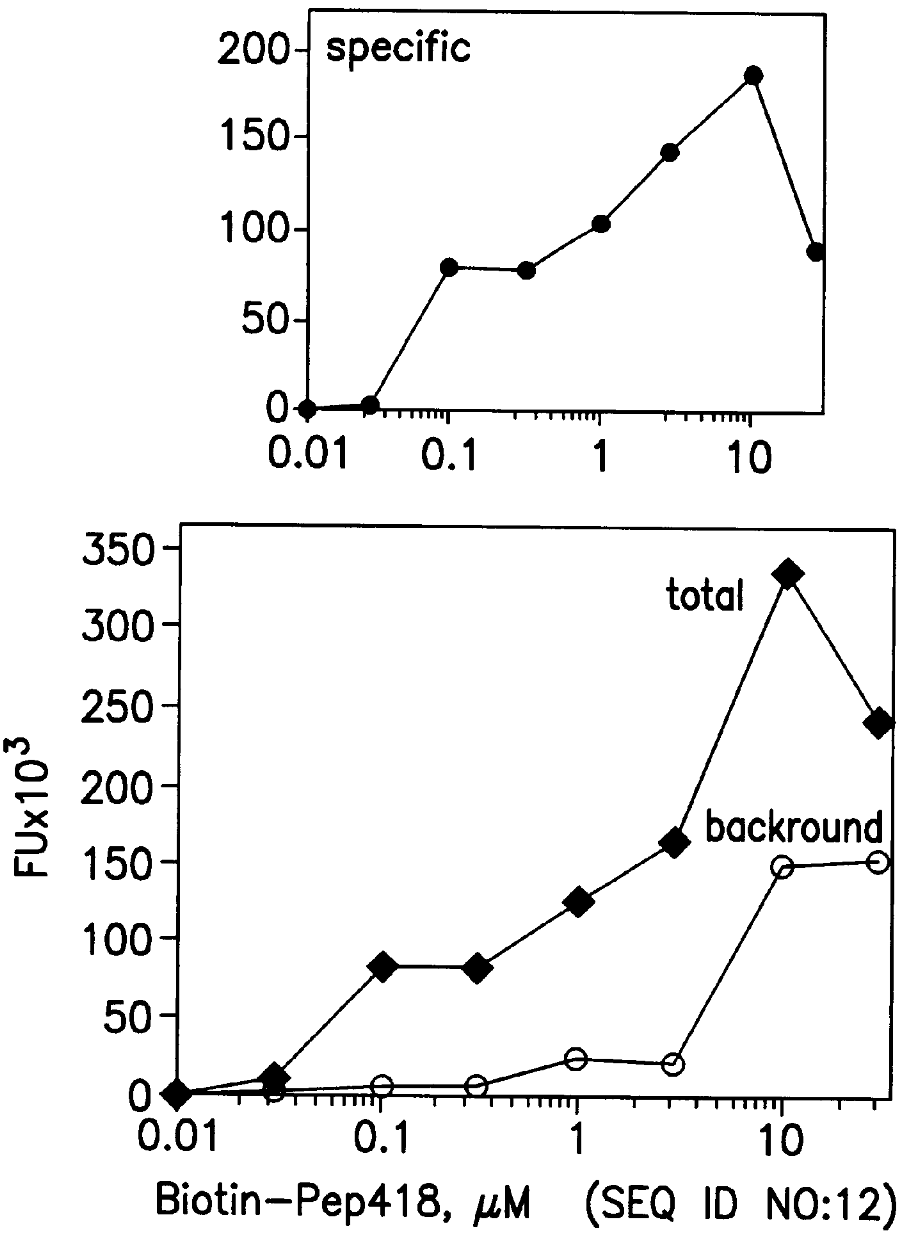
Figure 11C:
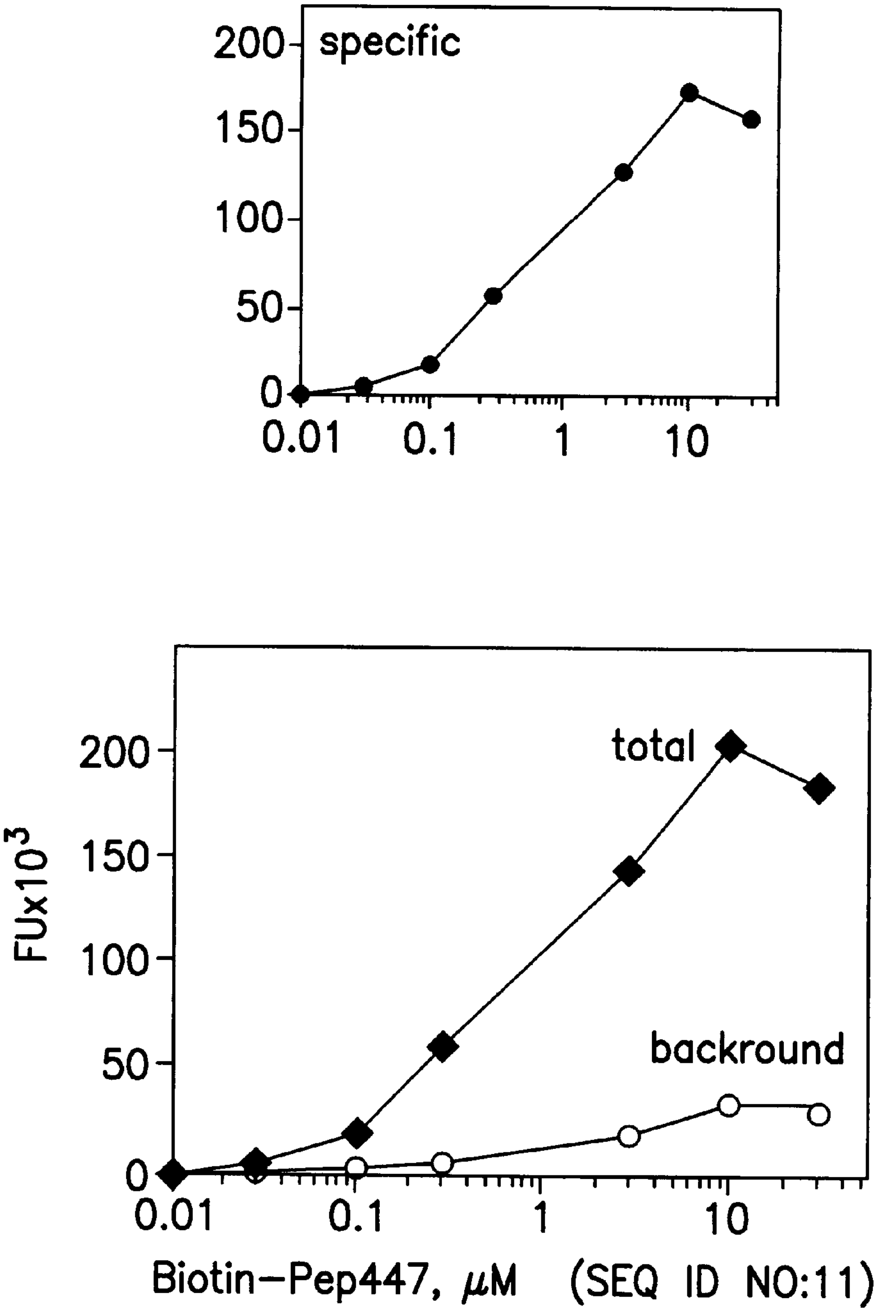
Figure 12A:
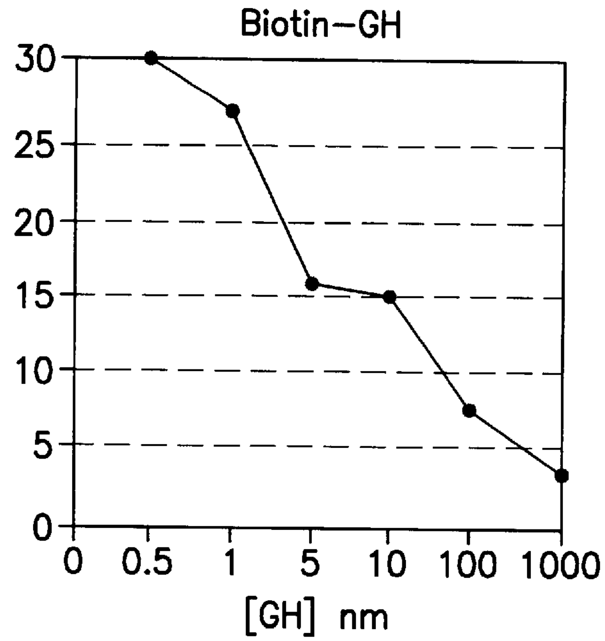
FIGS. 12A–F show competition of bLigand binding by other Agents. Wells were coated with rGHBP (100 ng) overnight. Binding to receptor after 2 hr incubation with bLigand in the presence of competing agent added 1 hr prior to bLigand addition is shown.
Figure 12B:
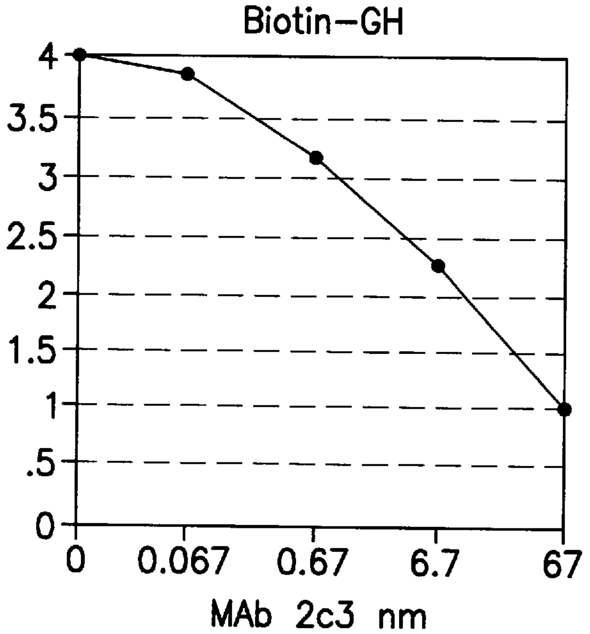
Figure 12C:
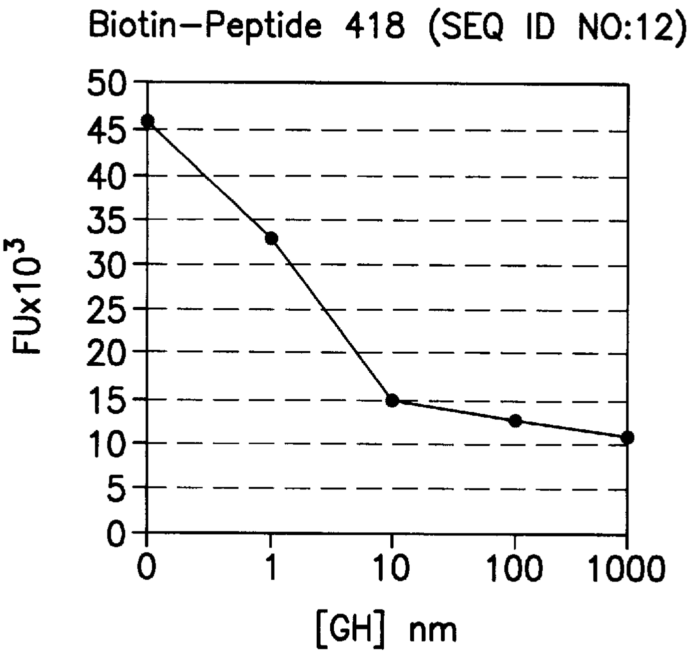
Figure 12D:
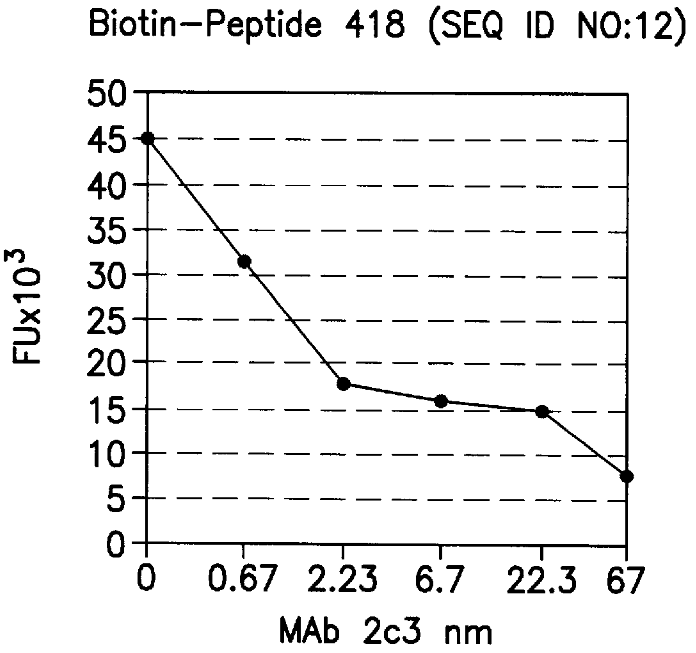
Figure 12E:
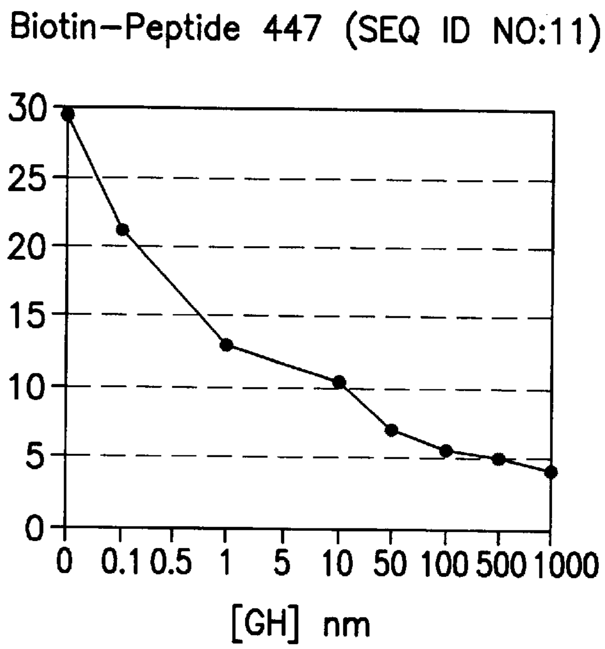
Figure 12F:
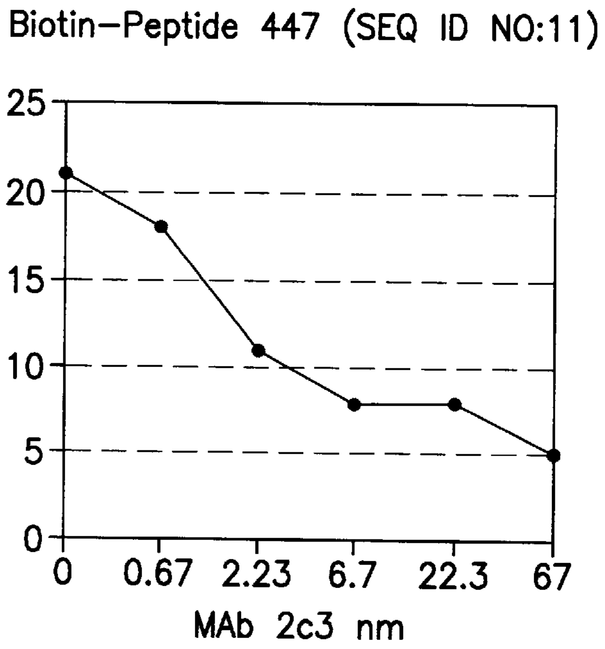

Dose response curves were conducted for bGH (from 0.01 to 1 μM) with wells coated with standard amounts of rGHBP (100 ng/well; FIG. 11). Specific binding to the active site of rGHBP, defined as the difference between binding in the absence and presence of excess GH shows increases from 0.01 to 100 nM but appears to saturate at 1 μM (FIG. 11A). Half maximum specific binding ($ED_{50}$) appears to be ~20 nM (Table II). The specific binding of a fixed concentration of bGH (2 nM) is inhibited by preincubation with non-biotinylated GH or the MAb 2C3 with half maximal inhibition values ($IC_{50}$) of 5–6 nM (FIG. 11A, B and Table II). The maximum inhibition is approximately equal, as expected with agents competitive for the same active site. Specific binding of bGH is also dependent upon input rGHBP. With 100 ng/well rGHBP coating (standard conditions), the ratio of specific to nonspecific binding (i.e., background binding) is close to 100/1 for bGH over the range 0.5 to 10 nM. Specific binding is detected at concentrations as low as 0.1 nM.

EXAMPLE 9

Specific Binding of H5-Related Peptides to rGHBP

Specific binding of bP#447 (SEQ ID NO:11) and bP#418 (SEQ ID NO:12) to rGHBP standard coated wells is likewise apparent. When tested from 0.001 to 30 μM background binding of bP#447 (SEQ ID NO:11) and bP#418 (SEQ ID NO:12) is greater than that of bGH at corresponding concentrations (compare FIG. 11A with B and C). Nevertheless, with both bP#447 (SEQ ID NO:11) and bP#418 (SEQ ID NO:12) there is also specific binding which appears to be saturable and shows respective $ED_{50}$s of 0.7–0.8 μM, respectively (Table II). Specific binding was evident with as little as 0.01–0.3 nM of these two bPs and the best signal to noise (i.e., background binding) ratio for both occurs at 0.3 μM with values of 20 to 40/1.

Previous analyses by ELISA and BIAcore indicate that the rank order of potency for binding to the rGHBP (Table I) is bP#447 (SEQ ID NO:11)=bP#418 (SEQ ID NO:12) >>H5WT (SEQ ID NO:8)≧bP#445 (SEQ ID NO:13). Binding analyses using the Time-Resolved Fluorescence Assay (TRFD) methodology shows that all bP tested are competed by excess GH or MAb2C3 and exhibit the same potency order (see FIG. 13). Even though receptors could not be saturated with H5WT (SEQ ID NO:8) or bP#445 (SEQ ID NO:13), the binding of the two best binders, bP#448 and bP#418 (SEQ ID NO:12), are 10 times better than H5WT (SEQ ID NO:8) or bP#445 (SEQ ID NO:13).

Figure 13:
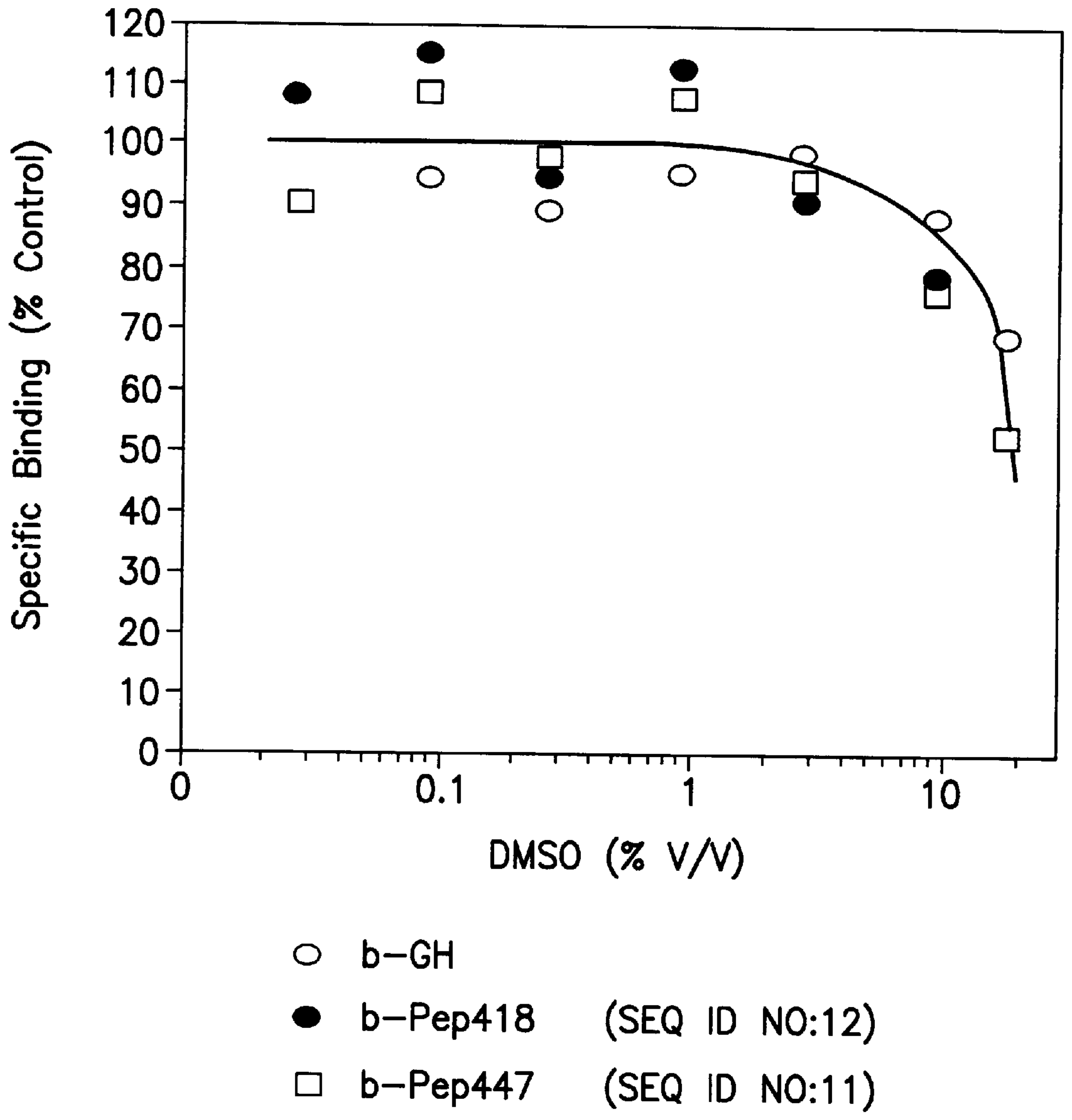
FIG. 13 shows the effect of DMSO on bLigand Binding to rGHBP. Wells were coated with rGHBP (100 ng/well) overnight. Total, background (plus 100 fold excess GH) and specific binding of 2 nM bGH, 0.3 $\mu$M bP#418 (SEQ ID NO:12), and 0.3 $\mu$M bP#447 (SEQ ID NO:11) was studied at increasing concentrations of DMSO. Data are given as % control specific binding seen in absence of DMSO.

In preparation for using this TRFD assay to examine chemical files for entities that bind to the active site of the GHR, the sensitivity of the assay to DMSO was investigated. This reagent is routinely used as a solvent for synthetic chemicals making up a chemical library and often reaches concentrations of 1% (v/v) in final HTS assays. DMSO was therefore added prior to ligand addition, and total, background and specific binding of bGH (3 nM), bP#447 (SEQ ID NO:11; 0.3 μM) and bP#418 (SEQ ID NO:12; 0.3 μM) were assayed in the presence of 0 to 20%(v/v) DMSO (FIG. 13). No statistically significant inhibition of any of these parameters up to 3% was found. At 10 and 20% DMSO there is a reduction in total, but not background binding indicating a loss in specific binding. DMSO $IC_{50}$ values appear to be >15% (v/v). These data indicate that either bP can be used at 0.3 μM on the presence of ≦3% DMSO.

EXAMPLE 10

Time-Resolved Fluorescence Assay rGHBP (50–200 μg/ml in 50 mM $NaHCO_3$) was coated onto low-fluorescence MaxiSorp (Nunc) plates (100 μl/well) overnight at 4° C. The plates were blocked with PBS containing 2% non-fat milk and 0.05% BSA for two hours at room temperature, followed by three PBS washes. For competitions, serial dilutions of unlabelled growth hormone (0.1 nM-100 nM) or MAb 2C3 (0.67–67 nM) were added to the plates (100 μl/well) and incubated at room temperature for 1–2 hours. Biotinylated peptide or biotinylated GH (10×concentrations) were incubated in blocking buffer for 30 minutes to decrease non-specific binding. Ten microliters of the 10×concentrated material was added to the plates and incubated at room temperature for 1 hour to overnight. The plates were then washed five times with Tris-buffered saline (pH 7.5) containing 0.1% Tween-(TTBS). To each well, 100 μl of europium-labeled streptavidin in DELFIA assay buffer (100 mM Tris-HCl, pH 7.8; 150 mM NaCl; 0.5% BSA; 0.05% bovine Ig; 0.05% NaN3; 0.01% Tween-20) was added and incubated for 1.5 hours at room temperature. The plates were then washed five times with TTBS and tapped dry. Subsequently, 100 μl of DELFIA enhancement solution (100 mM acetone-potassium hydrogen phthalate, pH 3.2; 15 mM 2-naphtyltrifluoroacetate; 50 mM tri(n-octyl)-phosphine oxide; 0.1% Triton X-100) was added to each well, and the plates were shaken for 10 minutes at room temperature. Fluorescence of each sample well was measured at 615 nm using a DELFIA 1234 fluorometer (EG&G Wallac). General procedure and references as described by Wallac and available in "Lanthanide labeling for time—resolved fluorometry": Wallac publication 1244-1126-03.

Two milligrams of human or bovine growth hormone were reacted with sulfo-NHS-LC-biotin (Pierce) following the manufacturer's instructions, and was desalted using a KwikSep column (MW cutoff 5,000; Pierce). The extent of biotin incorporation was determined using 2-(4'-hydroxyazobenzene) benzoic acid (HABA; Pierce) following the manufacturer's instructions.

Dose response of TRFD of Eu was studied in microtiter wells. Detection is linear over the range 0.2 to 200 fmol with a limit of detection (twice background) of 0.05 fmol. There are 6010 fluorescent units (FU) per fmol of Eu. Binding and detection of Eu(sa), (4.7 mol Eu/mol streptavidin) to wells coated with biotinylated BSA (bBSA) (6 mol biotin/mol BSA) is linear over the entire range tested. The specific fluorescent activity of streptavidin (sa):Eu (with 4 mol Eu/mol sa) is 28 KFU/fmol and the limits of detection (i.e., twice background) are 0.030 fmol. Coating with bGH was linear up to inputs of 200 ng/well and thereafter appeared to saturate at about 660 ng bGH per well. This is the expected amount based on the manufacture's information about protein saturation densities of these wells (Nunc manual). These studies show a limit of detection of bGH (i.e., twice background) of 0.05 fmol bGH. We next determined whether or not, and within what limits, this assay format detects specifically bound bGH (or bPeptides) to rGHBP coated wells.

The above results support the use of this assay procedure as a high throughput screen (HTS) for agents, with affinities for sites on the rat GHBP which bind GH. The studies show bP#447 (SEQ ID NO:11) and bP#418 (SEQ ID NO:12) bind in a dose-dependent, saturable manner and are blocked from binding by agents known to bind to the active site of the receptor. This competition is reproducible and easily quantified. Furthermore, the TRFD assay, which is automatable, is much more sensitive than is an ELISA. Finally, the assay is not influenced by DMSO if it is kept to <3% (v/v), a concentration of solvent most likely to be encountered in a HTS assay of large chemical libraries.

EXAMPLE 11

Agonistic and Antagonistic Activity of Peptides

Figure 14A:
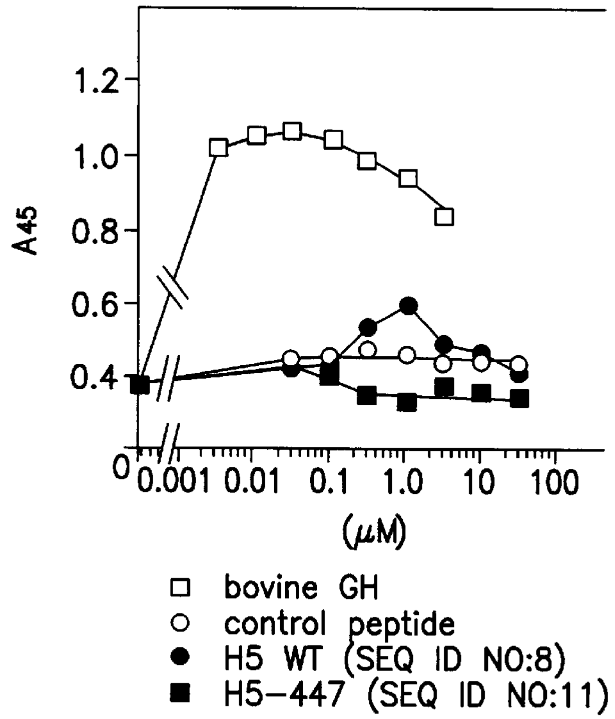
FIG. 14A shows agonistic activities of H5 (SEQ ID NO:8) and 447 (SEQ ID NO:11) tested by cell proliferation assays. Cells transfected with rat GHR (50,000 cells per well) were incubated with either bovine GH, H5 peptide (SEQ ID NO:8), 447 peptide (SEQ ID NO:11) or control peptide (SEQ ID NO:10) for 18 h at 37° C. Experiments were done in triplicate. Background signal $A_{450}$=0.15.
Figure 14B:
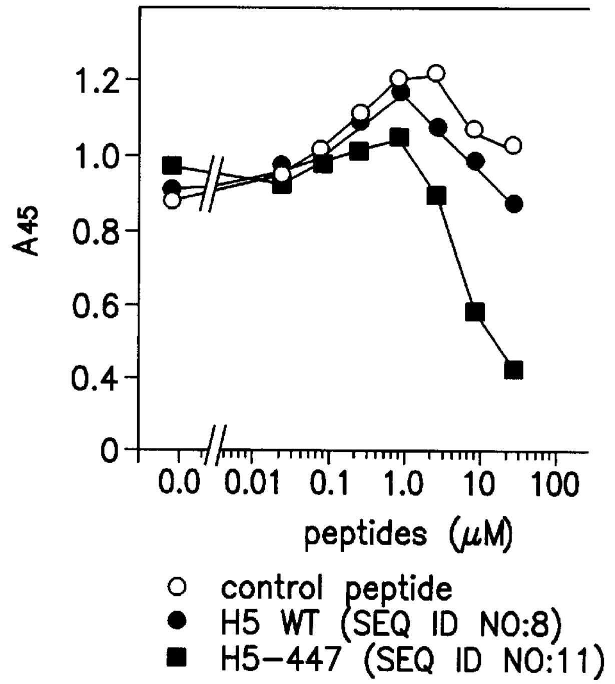
FIG. 14B shows antagonistic activities of H5 and 447 (SEQ ID NOS:8 and 11) tested by cell proliferation assays. Cells transfected with rat GHR (50,000 cells per well) containing 0.003 mM bovine GH were incubated with either control peptide (SEQ ID NO:10), H5 peptide (SEQ ID NO:8) or 447 peptide (SEQ ID NO:11) for 18 h at 37° C. Proliferation was measured using WST-1 reagent. The "*" symbol corresponds to the $A_{450}$ measurement for the cells incubated without GH.

Agonistic and antagonistic activities of the two peptides, H5WT (SEQ ID NO:8) and bP#447 (SEQ ID NO:11), were tested in FDC-1 cells stably transfected with the gene encoding the rat growth hormone receptor. The resulting cell line requires either IL-3 or GH for growth. These were grown in RPMI 1640 medium containing 10% FCS (fetal calf serum) and 20 units of IL-3 per ml. Antagonistic activity assays were performed in a total volume of 100 $\mu$l in 96 well plates (Riat bottom). Cells were seeded at 50,000 cells/well in 50 $\mu$l RPMI 1640 (without IL-3) medium containing horse serum instead of FCS to reduce background. To duplicate wells, 50 $\mu$l of either growth hormone or peptides at different concentrations was added, followed by incubation for 18 h in a $CO_2$ incubator. Assays to measure the antagonistic activity were performed in a total volume of 100 $\mu$l in 96 well plates. Either H5WT peptide (SEQ ID NO:8), bP#447 peptide (SEQ ID NO:11) or control peptide (SEQ ID NO:10) was added to cells containing 0.003 $\mu$M of bovine GH and incubated at 37° C. for 18 h in $CO_2$ incubator. Proliferation assays were performed using WST-1 reagent. The WST-1 tetrazolium salt (slightly red) is cleaved to formazan (dark red) by the succinate-tetrazolium reductase system is active only in viable cells. An increase in the number of cells results in an increase in the overall activity of the dehydrogenase, which results in a higher absorbance at 450 nm. Ten microliters of WST-1 reagent was added and the plates incubated for 1–4 h 37° C. Proliferation was measured by absorbance at 450 nm. The bP#447 peptide (SEQ ID NO:11) showed an antagonistic activity with an $IC_{50}$ of approximately 5 $\mu$M (FIG. 14). Control peptide (SEQ ID NO:10) or H5WT peptide (SEQ ID NO:8) showed no antagonistic activity at the concentrations tested. H5WT peptide (SEQ ID NO:8) showed partial agonistic activity, as indicated by a peak corresponding to 1 $\mu$M peptide concentration.

The following publications, some of which have been cited herein, are cited for general background information and are incorporated by reference in their entirety.

References

Baumbach W R, Homer D L, and Logan J S (1989). *Genes and Development* 3, 1199–1205.

Chen Y C J., Delbrook K, Dealwis C, Mimms L. Mushawar I K, and Mandecki W (1996). *Proc. Natl. Acad. Sci. USA* 93, 1997–2001.

Cwirla S E, Balasubramanian P. Duffin D J, Wagstrom C R, Gates C M, Singer S C, Davis A M, Tansik R L, Mattheakis L C, Boytos C M, Schatz P J, Baccanari D P, Wrighton N C, Barrett R W, and Dower W J (1997). *Science* 276, 1696–99.

Grihalde N D, Chen Y C, Golden A, Gubbins E, and Mandecki W (1995). *Gene* 166, 187–195.

Hopp T P, Prickett K S, Price V, Libby R T, March C J, Cerretti P, Urdal D L, and Conlon P J (1988). *Biotechnology* 6, 1205–1210.

Houghten R A (1985). *Proc. Natl. Acad. Sci. USA* 82, 5131–5135.

Kay B K, Adey N B, He Y S Manfredi J P, Mataragnon A H, and Fowlkes D. M (1993) *Gene* 128, 59–65.

Livnah O, Stura E A, Johnson D L, Middleton S A, Mulcahy L S, Wrighton N C, Dower W J, Jolliffe L K, and Wilson I A (1997). *Science* 273, 469–71.

Mandecki W, Brissette R. Carcamo J, Cheng W, Dedova O, Hsiao K C, Moghe A, Ravera M, Shen H, Tang P, and Blume A (1997). *Display Technologies-Novel Targets and Strateies*. P. Guttry (ed). International Business Communications, Inc., Southborough, Mass., pp. 231–254.

Renschler M F, Bhatt R R, Dower W J, and Levy R (1994). *Proc. Natl. Acad. Sci. USA* 91, 3623–3627.

Scott J K and Smith G P (1990). *Science* 249, 386–390.

Shukar, S B, Hajduk P J, Meadows R P, and Fesik S W (1996) *Science* 274, 1531–1534.

Souza S C, Frick G P, Wang X, Kopchick J J, Loborb R B, and Goodman H M (1995). *Proc. Natl. Acad. Sci. USA*, 82, 959–963.

Tompkins S M, Rota P A, Moore J C, and Jensen P E (1993), *J. Immunological Methods* 163, 209–216.

Wang B S, Lumanglas A A, Bona C A, and Moran T M (1996), *Mol Cellular Endocrinology* 116, 223–226.

Wrighton N C, Farrell F X, Chang R, Kashyap A K, Barbone F P, Mulcahy L S, Johnson D L, Barrett R W, Jolliffe L K, and Dower W J (1996). *Science* 273, 458–63.

Yanofsky S D, Balldwin D N, Butler J H, Holden F R, Jacobs J W, Balsubramanian P, Cinn J P, Cwirla S E, Petter-Bhatt E, Whitehorn E A, Tate E H, Akeson A, Bowlin T L, Dower W J, and Barrett R W (1996). *Proc. Natl. Acad. Sci. USA* 93, 7381–86.

What is claimed is:

1. An amino acid sequence which binds specifically to growth hormone receptor and comprises an amino acid sequence selected from the group consisting of SEQ ID NOS:2, 3, 5–8, 11–14, 16–78.

2. The amino acid sequence of claim 1, wherein the amino acid sequence binds to mammalian growth hormone receptor.

3. The amino acid sequence of claim 1, wherein the amino acid sequence binds to human growth hormone receptor.

4. A therapeutic composition comprising an amino acid sequence which binds specifically to growth hormone receptor and comprises an amino acid sequence selected from the group consisting of SEQ ID NOS:2, 3, 5–8, 11–14, 16–78.

5. The therapeutic composition of claim 4, wherein the amino acid sequence binds to human growth hormone receptor.

6. An amino acid sequence which binds specifically to growth hormone receptor and comprises amino acid sequence LCQRLGVGWPGWLSGWCAKK (SEQ ID NO:5).

7. A therapeutic composition comprising an amino acid sequence which binds specifically to growth hormone receptor and comprises amino acid sequence LCQRLGVGWPGWLSGWCAKK (SEQ ID NO:5).

8. An amino acid sequence which binds specifically to growth hormone receptor and comprises amino acid sequence LCQSWQVTWPGWLAGWCAKK (SEQ ID NO:6).

9. A therapeutic composition comprising an amino acid sequence which binds specifically to growth hormone receptor and comprises amino acid sequence LCQSWQVTWPGWLAGWCAKK (SEQ ID NO:6).

10. An amino acid sequence which binds specifically to growth hormone receptor and comprises amino acid sequence DYKDLCQRLGVGWPGWLSGWCA (SEQ ID NO:11).

11. A kit for identifying a compound which binds growth hormone receptor, comprising: a growth hormone receptor and amino acid sequence DYKDLCQRLGVGWPGWLSGWCA (SEQ ID NO:11).

12. A therapeutic composition comprising an amino acid sequence which binds specifically to growth hormone receptor and comprises amino acid sequence DYKDLCQRLGVGWPGWLSGWCA (SEQ ID NO:11).

13. An amino acid sequence which binds specifically to growth hormone receptor and comprises amino acid sequence LCQRLGVGWPGWLSGWCA (SEQ ID NO:76).

14. A kit for identifying a compound which binds growth hormnone receptor, comprising: a growth hormone receptor and amino acid sequence LCQRLGVGWPGWLSGWCA (SEQ ID NO:76).

15. A therapeutic composition comprising an amino acid sequence which binds specifically to growth hormone receptor and comprises amino acid sequence LCQRLGVGWPG-WLSGWCA (SEQ ID NO:76).

16. An amino acid sequence which binds specifically to growth hormone receptor and comprises amino acid sequence DYKDLCQSWQVTWPGWLAGWCA (SEQ ID NO:12).

17. A kit for identifying a compound which binds growth hormone receptor, comprising: a growth hormone receptor and amino acid sequence DYKDLCQSWQVTWPGW-LAGWCA (SEQ ID NO:12).

18. A therapeutic composition comprising an amino acid sequence which binds specifically to growth hormone receptor and comprises amino acid sequence DYKDL-CQSWQVTWPGWLAGWCA (SEQ ID NO:12).

19. An amino acid sequence which binds specifically to growth hormone receptor and comprises amino acid sequence LCQSWQVTWPGWLAGWCA (SEQ ID NO:70).

20. A kit for identifying a compound which binds growth hormone receptor, comprising: a growth hormone receptor and amino acid sequence LCQSWQVTWPGWLAGWCA (SEQ ID NO:70).

21. A therapeutic composition comprising an amino acid sequence which binds specifically to growth hormone receptor and comprises amino acid sequence LCQSWQVTWPG-WLAGWCA (SEQ ID NO:70).

22. An amino acid sequence which binds specifically to growth hormone receptor and comprises amino acid sequence DYKDLCQSLGVTYPGWLAGWCA (SEQ ID NO:8).

23. A kit for identifying a compound which binds growth hormone receptor, comprising: a growth hormone receptor and amino acid sequence DYKDLCQSLGVTYPGWLAG-WCA (SEQ ID NO: 8).

24. A therapeutic composition comprising an amino acid sequence which binds specifically to growth hormone receptor and comprises amino acid sequence DYKDLCQSLGV-TYPGWLAGWCA (SEQ ID NO:8).

25. An amino acid sequence which binds specifically to growth hormone receptor and comprises amino acid sequence LCQSLGVTYPGWLAGWCA (SEQ ID NO:16).

26. A kit for identifying a compound which binds growth hormone receptor, comprising: a growth hormone receptor and amino acid sequence LCQSLGVTYPGWLAGWCA (SEQ ID NO:16).

27. A therapeutic composition comprising an amino acid sequence which binds specifically to growth hormone receptor and comprises amino acid sequence LCQSLGVTYPG-WLAGWCA (SEQ ID NO:16).

28. An amino acid sequence which binds specifically to growth hormone receptor and comprises amino acid sequence DYKDLCQRLGVTWPGWLAGWCA (SEQ ID NO:14).

29. A kit for identifying a compound which binds growth hormone receptor, comprising: a growth hormone receptor and amino acid sequence DYKDLCQRLGVTWPGWLAG-WCA (SEQ ID NO: 14).

30. A therapeutic composition comprising an amino acid sequence which binds specifically to growth hormone receptor and comprises amino acid sequence DYKDLCQR-LGVTWPGWLAGWCA (SEQ ID NO:14).

31. An amino acid sequence which binds specifically to growth hormone receptor and comprises amino acid sequence LCQRLGVTWPGWLAGWCA (SEQ ID NO:44).

32. A kit for identifying a compound which binds growth hormone receptor, comprising: a growth hormone receptor and amino acid sequence LCQRLGVTWPGWLAGWCA (SEQ ID NO:44).

33. A therapeutic composition comprising an amino acid sequence which binds specifically to growth hormone receptor and comprises amino acid sequence LCQRLGVTWPG-WLAGWCA (SEQ ID NO:44).

* * * * *

UNITED STATES PATENT AND TRADEMARK OFFICE

CERTIFICATE OF CORRECTION

PATENT NO. : 6,387,879 B1 Page 1 of 1
DATED : May 14, 2002
INVENTOR(S) : Blume et al.

It is certified that error appears in the above-identified patent and that said Letters Patent is hereby corrected as shown below:

Title page, Item [54] and Column 1, line 1,
"COMPOUNDS THAT BIND GROWTH TO HORMONE RECEPTOR" should read -- COMPOUNDS THAT BIND TO GROWTH HORMONE RECEPTOR --.

Column 1,
Line 22, "35 ka" should read -- 35 kDa --.

Column 4,
Line 42, "rG1BP" should read -- rGHBP --.

Column 5,
Line 48, "OR" should read -- or --.

Column 12,
Line 3, "wig." should read -- FIG. --.

Column 13,
Lines 9-10, "(SEQ ID NO:12" should read -- (SEQ ID NO:12) --.

Column 14,
Line 51, "Tween-(TTBS)" should read -- Tween-20 (TTBS) --.

Column 16,
Line 41, "*Strateies*" should read -- *Strategies* --.

Column 49,
Line 5, "hormnone" should read -- hormone --.

Signed and Sealed this

Seventeenth Day of June, 2003

JAMES E. ROGAN
*Director of the United States Patent and Trademark Office*